US007087236B1

(12) United States Patent
Brayden

(10) Patent No.: US 7,087,236 B1
(45) Date of Patent: Aug. 8, 2006

(54) METHOD FOR INDUCING A CELL-MEDIATED IMMUNE RESPONSE AND IMPROVED PARENTERAL VACCINE FORMULATIONS THEREOF

(75) Inventor: David J. Brayden, Dublin (IE)

(73) Assignee: Merrion Research I Limited, Dublin (IE)

(*) Notice: Subject to any disclaimer, the term of this patent is extended or adjusted under 35 U.S.C. 154(b) by 0 days.

(21) Appl. No.: 09/386,266

(22) Filed: Aug. 31, 1999

Related U.S. Application Data

(60) Provisional application No. 60/098,760, filed on Sep. 1, 1998.

(51) Int. Cl.
*A61K 45/00* (2006.01)
*A61K 39/295* (2006.01)
*A61K 39/116* (2006.01)
*A61K 39/00* (2006.01)
*A61K 39/02* (2006.01)

(52) U.S. Cl. .............................. 424/280.1; 424/201.1; 424/203.1; 424/184.1; 424/234.1; 424/253.1; 424/254.1; 514/2; 530/825; 530/350

(58) Field of Classification Search ............ 424/253.1, 424/254.1, 240.1, 184.1, 499, 234.1, 9.2, 424/9.322, 9.611, 203.1, 426, 455, 486, 489, 424/444, 491, 470, 280.1, 201.1; 514/885; 530/350, 825
See application file for complete search history.

(56) References Cited

U.S. PATENT DOCUMENTS

| | | | | |
|---|---|---|---|---|
| 5,075,109 | A | 12/1991 | Tice et al. | 424/88 |
| 5,362,478 | A | 11/1994 | Desai et al. | 424/9 |
| 5,393,527 | A | 2/1995 | Malick et al. | 435/7.1 |
| 5,417,986 | A | 5/1995 | Reid et al. | 424/499 |
| 5,439,686 | A | 8/1995 | Desai et al. | 424/451 |
| 5,441,739 | A | 8/1995 | Kossovsky et al. | 424/400 |
| 5,529,777 | A | 6/1996 | Andrianov et al. | 424/84.1 |
| 5,603,960 | A | 2/1997 | O'Hagan et al. | 424/501 |
| 5,631,263 | A | 5/1997 | Portoghese et al. | 514/279 |
| 5,674,534 | A | 10/1997 | Zale et al. | 424/501 |
| 5,709,879 | A | 1/1998 | Barchfeld et al. | 424/450 |
| 5,807,757 | A | 9/1998 | Andrianov et al. | 436/535 |
| 5,871,747 | A | 2/1999 | Gengoux-Sedlik et al. | 424/208.1 |
| 5,885,586 | A | 3/1999 | Eckhardt et al. | 424/240.1 |
| 5,885,587 | A | 3/1999 | Eckhardt et al. | 424/240.1 |
| 5,895,655 | A | 4/1999 | Eckhardt et al. | 424/240.1 |
| 5,897,867 | A | 4/1999 | Eckhardt et al. | 424/240.1 |
| 6,004,763 | A | 12/1999 | Gengoux et al. | 435/7.24 |
| 6,024,983 | A * | 2/2000 | Tice et al. | 424/501 |
| 6,056,964 | A * | 5/2000 | Rook et al. | 424/248.1 |
| 6,309,669 | B1 | 10/2001 | Setterstrom et al. | 424/486 |
| 6,372,227 | B1 * | 4/2002 | Garcon et al. | 424/283.1 |

FOREIGN PATENT DOCUMENTS

| | | | |
|---|---|---|---|
| EP | 0 154 902 | | 2/1985 |
| EP | 0 266 119 | B1 | 10/1987 |
| EP | 0 333 523 | | 3/1989 |
| EP | 0 706 792 | | 3/1989 |
| EP | 0 484 621 | A3 | 5/1991 |
| EP | 0 686 630 | B1 | 6/1995 |
| EP | 0 737 472 | A1 | 3/1996 |
| WO | WO 86/06635 | | 11/1986 |
| WO | WO 90/04963 | | 5/1990 |
| WO | WO 92/19263 | | 11/1992 |
| WO | WO 93/20843 | | 4/1993 |
| WO | WO 93/21950 | | 11/1993 |
| WO | WO 94/06472 | | 3/1994 |
| WO | WO 94/08588 | | 4/1994 |
| WO | WO 94/09898 | | 5/1994 |
| WO | WO 94/15636 | | 7/1994 |
| WO | WO 94/21289 | | 9/1994 |
| WO | WO 95/02416 | | 1/1995 |
| WO | WO 95/11008 | | 4/1995 |
| WO | WO 95/11010 | | 4/1995 |
| WO | WO 95/13838 | | 5/1995 |
| WO | WO 95/17167 | | 6/1995 |
| WO | WO 95/28486 | * | 10/1995 |
| WO | WO 95/35097 | | 12/1995 |
| WO | WO 96/14876 | | 5/1996 |
| WO | WO 96/20698 | | 7/1996 |
| WO | WO 97/17613 | | 5/1997 |
| WO | WO 97/31691 | | 9/1997 |
| WO | WO 97/32572 | | 9/1997 |
| WO | WO 98/51325 | | 11/1998 |
| WO | WO 98/51825 | | 11/1998 |
| WO | WO 98/58668 | | 12/1998 |

(Continued)

OTHER PUBLICATIONS

Cahill et al. Vaccine 13: 455-462, 1995.*
Shahin et al. Infect Immun. 63: 1195-1200, 1995.*
Mills et al. Infect Immun. 61: 399-410, 1993.*
Eldridge et al. J. Controlled Release 11: 205-214, 1990.*
Moore et al. Vaccine 13: 1741-1749, 1995.*
Nixon et al. Vaccine 14: 1523-1530, 1996.*

(Continued)

*Primary Examiner*—S. Devi
(74) *Attorney, Agent, or Firm*—Synnestvedt & Lechner LLP

(57) ABSTRACT

A method of inducing either a $T_H1$ polarized immune response, a $T_H2$ polarized immune response or a combined $T_H1$ and $T_H2$ response to an antigen and associated vaccine formulations are disclosed. A method is provided for inducing a polarized $T_H1$ response by parenteral administration of microparticles sized such that at least 50% of the microparticles are less than 5 μm. The microparticles containing antigen entrapped or encapsulated by a biodegradable polymer. Additionally, a method is provided for inducing a polarized $T_H2$ response by parenteral administration of nanoparticles sized such that at least 50% of the nanoparticles are less than 600 nm, the nanoparticles containing antigen entrapped or encapsulated by a biodegradable polymer. Vaccine formulations containing the *B. pertussis* antigens PTd, FHA or a combination of PTd and FHA are provided.

10 Claims, 10 Drawing Sheets

OTHER PUBLICATIONS

Jones et al. Behring Inst. Mitt. 98: 220-228, Feb. 1997.*
Jones et al. Vaccine 1: 675-681, 1995.*
Maloy et al. Immunology 8: 661-667, 1994.*
O'Hagan. In: New Generation of Vaccines, (Ed) M.M. Levine. Marcel Dekker Inc. Chapter 17, 2nd Edition, pp. 215-228, 1997.*
Gregoriadis, G., "Preparation of Liposomes", Liposome Technology, vol. 1, Clinical Research Centre, Middlesex, England, pp. 122-129.
Ostro, M.J., "Liposomes", From Biophysics to Therapeutics, The Liposome Company, Princeton, New Jersey, pp. 73-108.
Rechtman, D., "Oral Administration of Tetanus Vaccine—Issues Related to Acceptance, Target Populations and Clinical Trials", PharmaMedical Consultants International, pp. 1-11.
Preis, I. et al., "A Single-Step Immunization by Sustained Antigen Release", J. Immunol Methods, vol. 28, No. 1-2, 1979, pp. 193-197.
Uchida et al , "Oral Delivery of Poly(lactide-co-glycolide) Microspheres Containing Ovalbumin as Vaccine Formulation: Particle Size Study" Biol. Pharm. Bull., vol. 17, No. 9, Sep. 1994, pp. 1272-1276.
Maloy, K. et al., "Induction of Mucosal and Systemic Immune Responses by Immunization with Ovalbumin Entrapped in Poly(lactide-co-glycolide) Microparticles", Immunology, vol. 81, 1994, pp. 661-667.
Ulrich, J. et al., "Monophosphoryl Lipid A as an Adjuvant—Past Experiences and New Directions", Ribi ImmunoChem Research, Inc., Hamilton, Montana 59840, Chapter 21, pp. 495-523, 1995.
Moore, A. et al., "Immunization with a soluble recombinant HIV protein entrapped in biodegradable microparticles induces HIV-specific $CD8^+$ cytotoxic T lymphocytes and $CD4^+$ Th1 cells", Vaccine, vol. 18, Oct. 29, 1995, pp. 1-11.
Men, Y. et al., "A single administration of tetanus toxoid in biodegradable microspheres elicits T cell and antibody responses similar or superior to those obtained with aluminum hydroxide", Vaccine, vol. 13, No. 7, 1995, pp. 683-689.
Desai, M.P. et al., "Gastrointestinal uptake of biodegradable microparticles: effect of particle size", Pharmaceutical Research, vol. 13, No. 12, 1996, pp. 1838-1845.
Marinaro, M. et al., "Use of Intranals IL-12 to Target Predominantly Th1 Responses to Nasal and Th2 Responses to Oral Vaccines Given with Cholera Toxin[1]", The Journal of Immunology, 1999, pp. 114-121.
Jones, D.H. et al., "Orally Administered Microencapsulated *Bordetella pertussis* Fimbriae Protect Mice from *B. pertussis* Respiratory Infection", Infection and Immunity, vol. 64, No. 2, Feb. 1996, pp. 489-494.
Lee, V., "Pharmaceutical Research", An Official Journal of the American Association of Pharmaceutical Scientists, vol. 13, No. 9, Sep. 1996, pp. S237-S242.
Rubas, W. et al., "An Integrated Method to Determine Epithelial Transport and Bioactivity of Oral Drug Candidates in Vitro", Pharmaceutical Research, vol. 13, No. 1, 1996, pp. 23-25.

McClean, S. et al., "Binding and Uptake of Biodegradable Poly-DL-Lactide Micro- and Nanoparticles in Intestinal Epithelia", European Journal of Pharmaceutical Sciences, 1997, pp. 3-11.
Nugent, J. et al., "Design and delivery of non-parenteral vaccines", Journal of Clinical Pharmacy and Therapeutics, vol. 23, No. 4, Aug. 1998, pp. 257-285.
Brayden, D.J., et al., "Novel oral drug delivery gateways for biotechnology products: polypeptides and vaccines". Pharmaceuticals Science and Technology Today, vol. 1, No. 7, Oct. 1998 pp. 291-299.
Singh, et al., "The preparation and characterization of polymeric antigen delivery systems for oral administration". Adv. Drug Delivery Rev, Dec. 1998, vol. 34, No. 2-3, pp. 285-304.
Singh, et al., "Controlled release microparticles as a single dose diphtheria toxoid vaccine: immunogenicity in small animal models", Vaccine, Feb. 1998, vol. 16, No. 4, 1998, pp. 346-352.
Newman, K. et al., "Delivery of MUC1 Mucin Peptide by Poly(d,l-lactic-co-glycolic acid) Microspheres Induces Type 1 T Helper Immune Responses", Journal of Pharmaceutical Sciences, vol. 87, No. 11, Nov. 1998, pp. 1421-1428.
Harokopakis, E. et al., "Effectiveness of Liposomes Possessing Surface-Linked Recombinant B Subunit of Cholera Toxin as an Oral Antigen Delivery System", Infection and Immunity, Sep. 1998, vol. 66, No. 9, pp. 4299-4304.
Croyle, M. et al., "In-Vitro and in-Vivo Assessment of Adenovirus 41 as a vector for gene delivery to the intestine", Gene Therapy, vol. 5, 1998, pp. 645-654.
Rook, G. et al., "Give Us This Day our Daily Germs", Immunology Today, vol. 19, No. 3, Mar. 1998, pp. 113-120.
Ryan, M. et al., "Distinct T-cell subtypes induced with whole cell and accellar pertussis vaccines in children", Immunology, vol. 93, 1998, pp. 1-10.
Newman, K. et al., "Ovalbumin Peptide Encapsulated in Poly(d,l lactic-co-glycolic acid) Microspheres is Capable of Inducing a T Helper Type 1 Immune Response", Journal of Controlled Release, vol. 54, No. 1, 1998, pp. 49-59.
Cleland, J. "Single-administration vaccines: controlled-release technology to mimic repeated immunizations", Tibtech, Jan. 1999, vol. 17, pp. 25-29.
Boyaka, P. et al., "IL-12 Is an Effective Adjuvant for Induction of Mucosal Immunity", The Journal of Immunology, 1999, pp. 122-128.
Tobio, M. et al., "A Novel System Based on a Poloxamer/PLGA Blend as a Tetanus Toxoid Delivery Vehicle", Pharmaceutical Research, vol. 16, Nov. 5, 1999, pp. 682-688.
Shroff, K. et al., "Potential for Plasmid DNAs as Vaccines for the New Millennium", PSTT, vol. 2, No. 5, May 1999, pp. 205-212.
Search Report for Application PCT/IE 99/00087.
Kissel, T., et al., "Injectable Biodegradable Microspheres for Vaccine Delivery" Microparticulate Systems for the Delivery of Proteins and Vaccines, Marcel Dekker, Inc. (S. Cohen, et al., Editors), 1996, pp. 51-87.

* cited by examiner

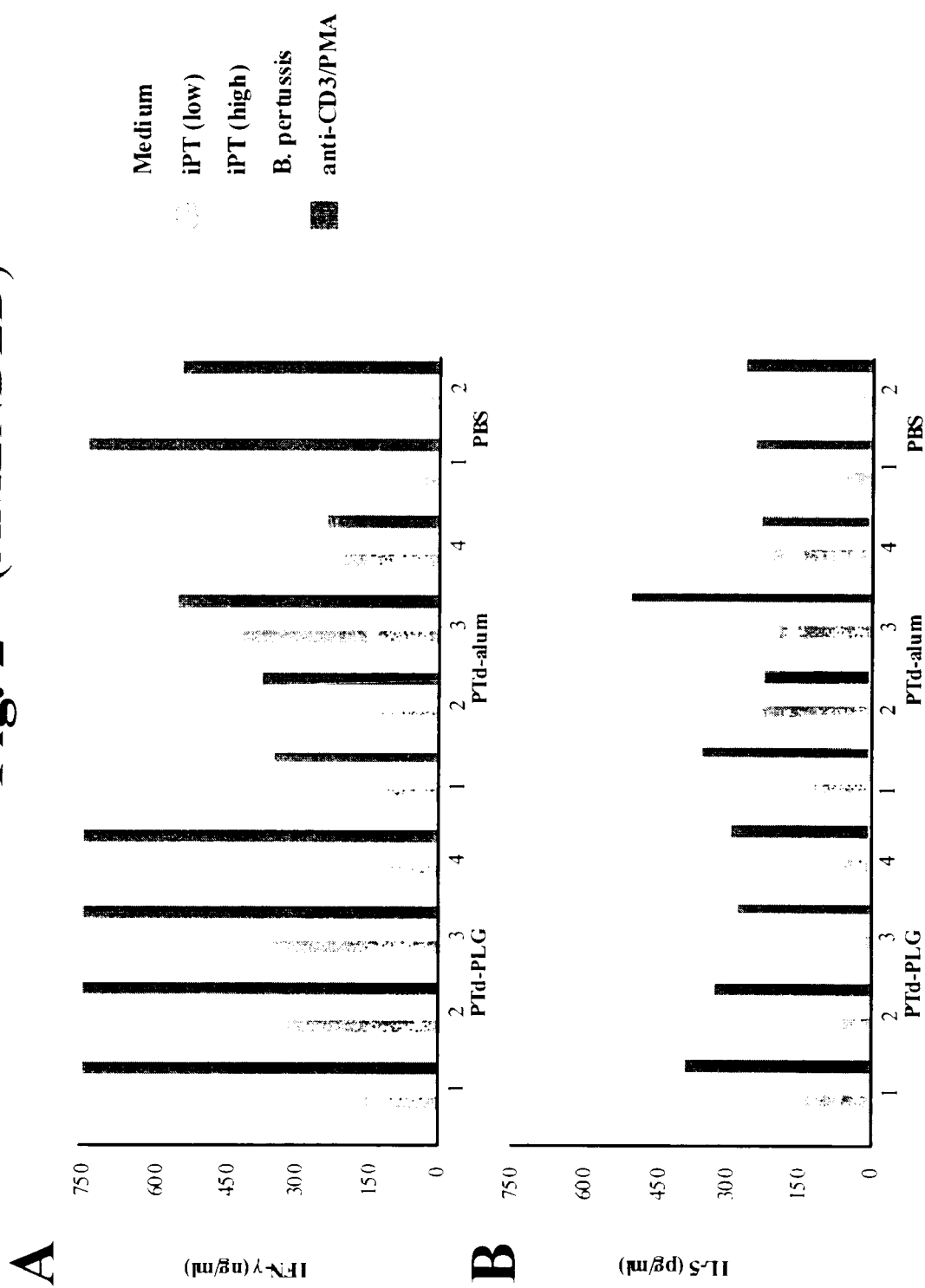
Fig. 2 (AMENDED)

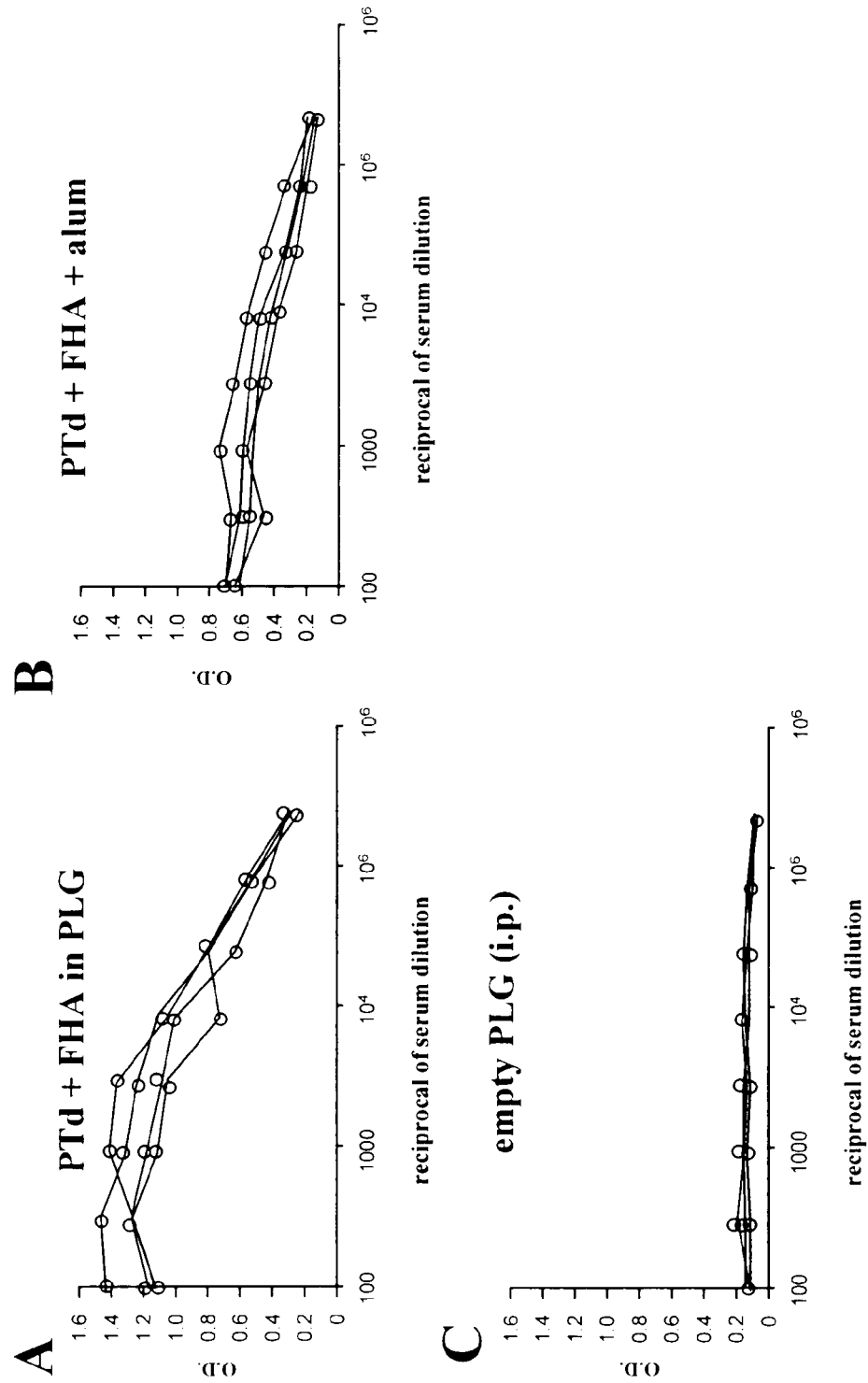
Fig. 4 (AMENDED)

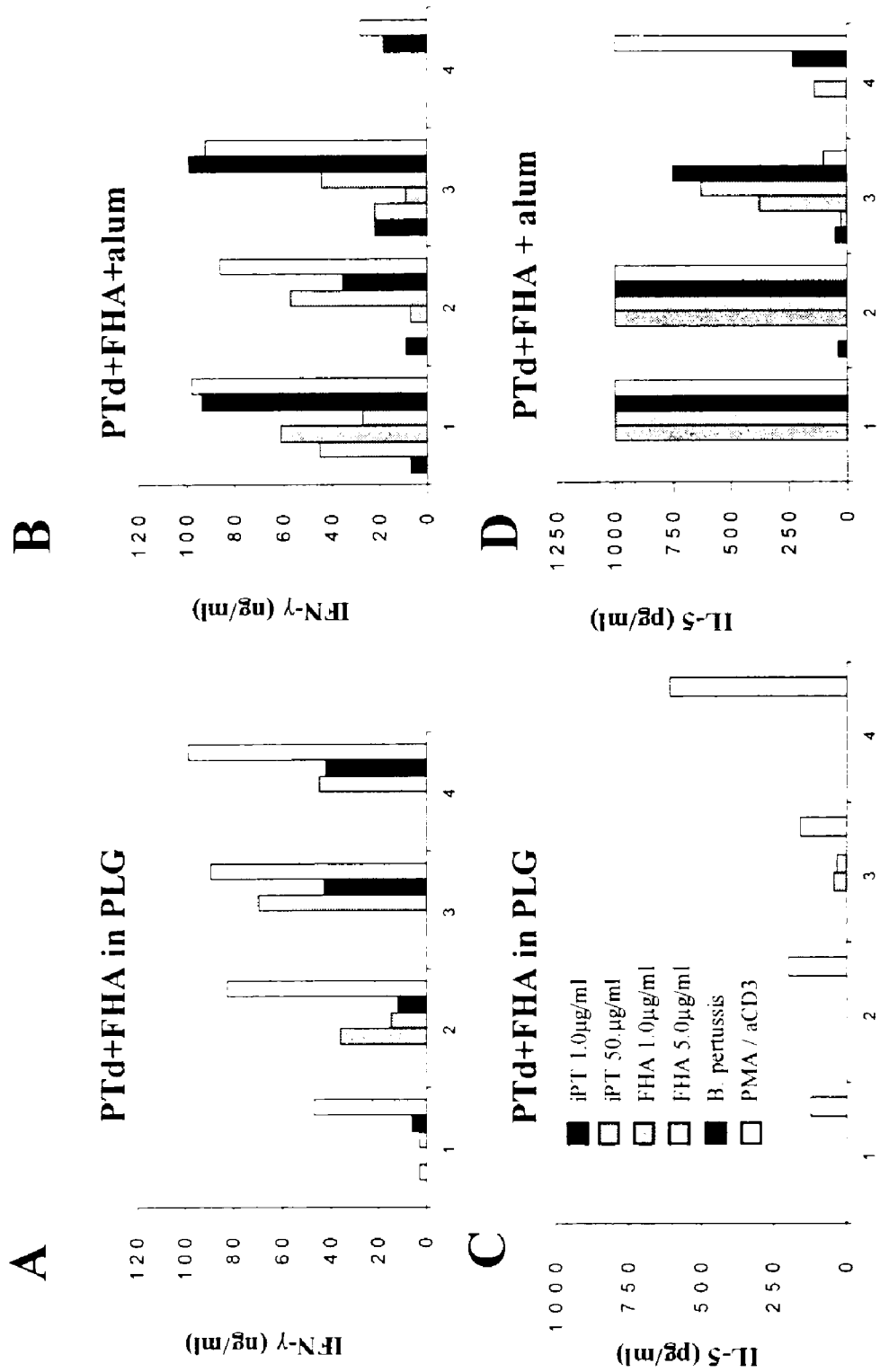
Fig. 5 (AMENDED)

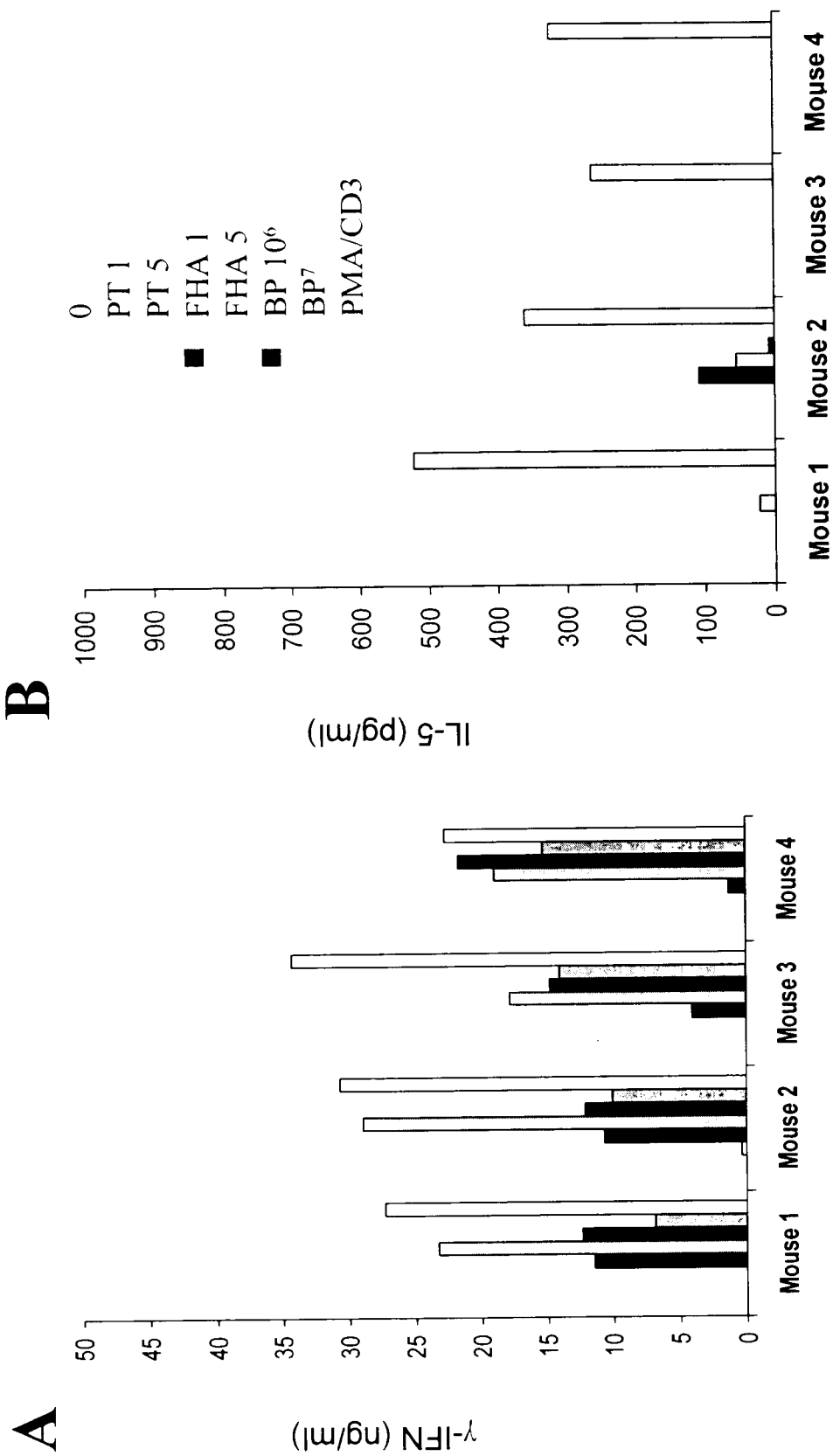
Figure 6 (AMENDED)

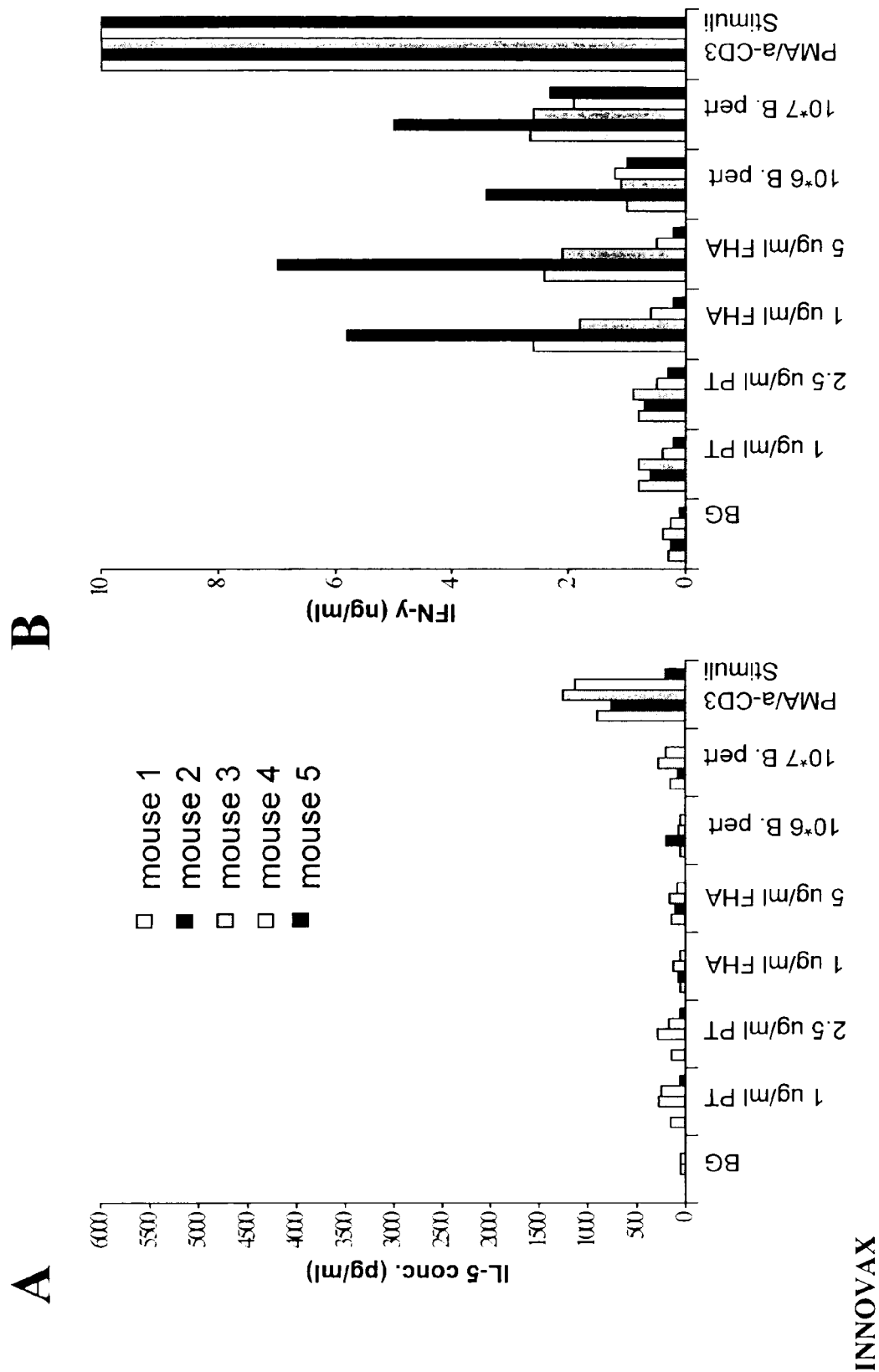
Fig. 9 (AMENDED)

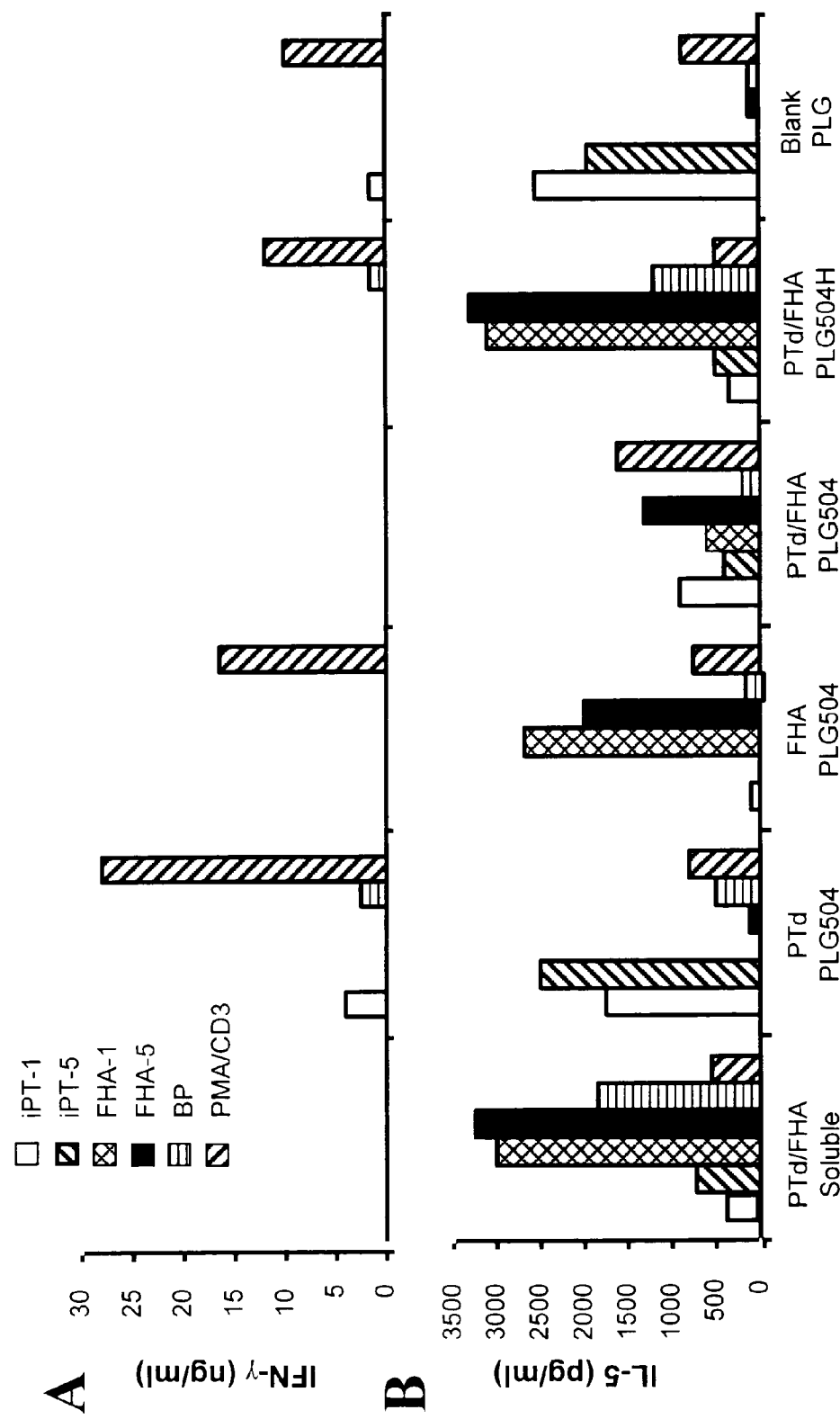
Fig. 10 (AMENDED)

METHOD FOR INDUCING A CELL-MEDIATED IMMUNE RESPONSE AND IMPROVED PARENTERAL VACCINE FORMULATIONS THEREOF

This application claims the benefit of U.S. Provisional Application No. 60/098,760, filed Sep. 1, 1998.

FIELD OF THE INVENTION

The present invention relates to vaccine formulations and to methods for inducing an immune response that is polarised in favour of either a cell-mediated $T_H1$ immune response, a humoral $T_H2$ immune response or a combined $T_H1$ and $T_H2$ response. In particular, the present invention relates to parenteral microparticulate and nanoparticulate vaccine formulations comprising antigens entrapped or encapsulated within polymer particles.

DESCRIPTION OF THE PRIOR ART

Controlled release antigen delivery systems have attracted considerable interest in the continuing search for vaccine carriers. The effectiveness of polymer matrices in the sustained release of antigen was first demonstrated in 1979 with the entrapment of bovine serum albumin in a non-degradable ethylene-vinyl acetate copolymer pellet for subcutaneous implantation [Preis et al, J. Immunol. Methods 28, 193–197 (1979)]. This composition induced an antibody response for six months after administration and gave antibody levels similar to two injections of the same total amount of antigen in complete Freund's adjuvant.

More recently aluminium salts (see for example WO 94/15636 (CSL Ltd.)) and biodegradable polymers such as poly (L-lactide) (hereinafter PLA) and poly (DL-lactide-co-glycolide) (hereafter PLGA) have been used as carriers for vaccine antigens. WO 95/11008 (Genentech Inc.) discloses the use of PLGA microspheres for encapsulating an antigen in which the ratio of lactide to glycolide in the microspheres ranges from 100:0 to 0:100 weight percent, the inherent viscosity of the PLGA polymers ranges from 0.1–1.2 dl/g and the median diameter of the microspheres ranges from 20–100 μm. The antigen can be continuously released from the microspheres over an extended period in a triphasic pattern. A method for encapsulating antigens in microspheres is also disclosed.

Eldridge et al., J. Controlled Release 11, 205–214 (1990) report that the oral administration of biodegradable PLA or PLGA microspheres containing the staphylococcal enterotoxin B (SEB) vaccine are absorbed into the Peyer's patches of the small intestine. Uptake is restricted to particles ≦10 μm in diameter. The majority of microspheres <5 μm were observed to be transported to systemic lymphoid tissue (such as the spleen) where the released antigen stimulated a serum antibody response. The majority of those particles >5 μm were found to be retained in the Peyer's patches. EP 0 266 119 (The UAB Research Foundation & Southern Research Institute) teaches an oral composition comprising a bioactive agent, such as an antigen, encapsulated in a biodegradable polymer excipient to form a microcapsule less than or equal to 10 μm that is capable of being taken up selectively by the Peyer's patch. Similarly, EP 0 333 523 (The UAB Research Foundation & Southern Research Institute) and EP 0 706 792 divided therefrom, teach compositions for delivery of a bioactive agent, such as an antigen, to the muscosally associated lymph tissue (MALT), comprising microcapsules having sizes between 1–5 and 5–10 μm for selective absorption and retention in MALT.

EP 0 686 030 (Gesellschaft zur Forderung der Industrieorientierten Forschung) teaches a method of potentiating an immune response by embedding a model antigen in a biodegradable biopolymer and injecting it in the form of a dispersion in order to trigger a humoral and cellular response. In this instance PLGA entrapped antigens were shown to elicit long lasting T helper, antibody and cytotoxic T cell responses.

Moore et al., Vaccine 18 1741–1749 (1995) disclosed that HIV gp120 entrapped in PLGA solvent evaporated microspheres can induce cytolytic activity (CTL) in mice splenic T cells upon nasal, s.c. or i.p. administration. For this antigen, anti-HIV specific CD4+ and CD8+ T cells were induced leading to induction of $T_H1$ cells and CTL respectively. In the case of i.p. ovalbumen (OVA) immunisation, Maloy et al., Immunology 81, 661–667 (1994) disclose that a single s.c. immunization with OVA-PLGA microspheres primed significant OVA-specific responses and strong OVA-specific CTL responses were found after i.p immunisation in mice. Newman et al., J. Controlled Release, 54, 49–59 (1998) disclose the use of OVA peptide encapsulated in PLGA microspheres for inducing a $T_H1$ type immune response in mice after s.c. delivery.

Distinction between the types of immune response in terms of $T_H1$ (cell-mediated) and $T_H2$ (humoral/antibody) type responses is important for protection against infectious diseases induced by intracellular pathogens or extracellular toxins respectively. The division of CD4+ lymphocytes into $T_H2$ according to antibody sub-class and cytokine profile has led to attempts to classify adjuvants accordingly. For instance, aluminium hydroxide (also referred to as alum) is considered to have a higher capacity for inducing $T_H2$ rather than $T_H1$ immunity [see, e.g., Men et al., Vaccine 13, 683–689 (1995)]. U.S. Pat. No. 5,417,986 (US Army) describes the loading of PLGA microspheres with antigens such as CFA (complete Freund's adjuvant) and HepB sAg (hepatitis B surface antigen) and injected to give both antibodies and T cell proliferation in animals.

Review of the above cited references and other literature in the area shows that there is no general method for predicting or anticipating the nature of the immune response induced by an antigen in combination with a given adjuvant.

With respect to *Bordetella pertussis*, the fimbrae, filmentous hemaglutinin (FHA), inactivated *pertussis* toxin (PTd) and pertactin antigens have all been entrapped in PLGA microspheres, administered individually by a variety of routes and have been shown to protect against infection in response to challenge in a mouse model of *pertussis* (see, e.g., Shahin et al., Infection and Immunity 63, 1195–1200 (1995); Jones et al., Infection and Immunity 64, 489–494 (1996); Cahill et al., Vaccine 13, 455–462 (1995)). WO 93/21950 (Roberts and Dougan) teaches that the antigens FHA and pertactin are immunogenic as a mixture or when entrapped in PLGA and delivered to mucosal sites. Singh et al., Vaccine 16, 346–352 (1998) describe that two antigens entrapped simultaneously in the same polymer particles can induce antibody responses to each agent in rats after parenteral delivery. There is evidence that the mouse model of aerolised *pertussis* infection correlates with *pertussis* vaccine efficacy in children [Mills et al., Infection and Immunity 66, 594–602 (1998)] and that $T_H1$ cells play an important role in bacterial clearance [Mills et al., Infection and Immunity 61, 399–410 (1993)]. Further work by Ryan et al., Immunology 93, 1–10 (1998) indicates that the long-term protective immunity of a potent whole cell *pertussis* vaccine in children is largely mediated by $T_H1$ cells. Accellular *pertussis* vaccines appear to involve a mixed population of $T_H1$ and $T_H2$ cells and their long term efficacy is unknown.

Despite the abovementioned prior art, the ability to predict and control the type of immune response produced by a given vaccine formulation remains a goal central to immunology research. This is particularly true given the variation from disease to disease of the relative importance of $T_H1$ and $T_H2$ components of the immune response. For example, $T_H1$ response can assist in cytotoxic T cell activity which is important in clearances of viruses, intracellular pathogens and some cancers.

Therefore, it is an object of the present invention to provide a vaccine formulation which will elicit a significant and reproducible polarised $T_H1$ immune response in vivo. It is also an object of this invention to provide methods to enhance the $T_H1$ T cell response compared to the $T_H2$ response. Additionally, it is an object of the present invention to provide a vaccine formulation which will elicit a significant and reproducible polarised $T_H2$ immune response in vivo and methods to enhance the $T_H2$ T cell response compared to the $T_H1$ response.

It is an another object of the present invention to provide a parenteral vaccine formulation directed at a particular agent such as an infectious agent which, after administration to the subject, is capable of providing protective immunity against the agent.

Further objects of the present invention include an improved composition for use in the preparation of a *B. pertussis* vaccine and a method for the vaccination against *B. pertussis*.

SUMMARY OF THE INVENTION

It has now been surprisingly found that polarisation of the $T_H1$ immune response over the $T_H2$ immune response or that polarisation of the $T_H2$ immune response over the $T_H1$ immune response can be induced by the choice of parenteral administration of microparticles or nanoparticles comprising antigen entrapped or encapsulated in a biodegradable polymer using a suitable combination of polymer type, loading method, morphology and size.

Furthermore, it has been found that a vaccine formulation designed for a particular agent such as an infectious agent and containing microparticles or nanoparticles comprising antigen entrapped or encapsulated in a biodegradable polymer can, in addition to inducing T cell proliferation, yield protective immunity against the infectious agent.

Accordingly, the present invention provides a method of inducing a $T_H1$ polarised immune response to an antigen(s), comprising parenterally administering to a subject, such as a mammal and preferably a human, microparticles sized such that at least 50% of the microparticles are less than 5 μm, preferably less than 3 μm, the microparticles comprising the antigen(s) entrapped or encapsulated by a biodegradable polymer. A vaccine formulation for parenteral administration comprising microparticles sized such that at least 50% of the microparticles are less than 5 μm, preferably less than 3 μm, the microparticles comprising antigen entrapped or encapsulated by a biodegradable polymer is also provided.

Additionally, the present invention provides a method of inducing a $T_H2$ polarised immune response to an antigen(s), comprising a parenterally administering to a subject, such as a mammal and preferably a human, nanoparticles sized such that at least 50% of the nanoparticles are less than 600 nm, preferably less than 500 nm, the nanoparticles comprising the antigen(s) entrapped or encapsulated by a biodegradable polymer. A vaccine formulation for parenteral administration comprising microparticles sized such that at least 50% of the nanoparticles are less than 600 nm, preferably less than 500 nm, the nanoparticles comprising antigen entrapped or encapsulated by a biodegradable polymer is also provided.

The present invention also provides a method of inducing both a potent $T_H1$ and $T_H2$ immune response to an antigen(s), comprising parenterally administering to a subject, such as a mammal and preferably a human, (1) microparticles sized such that at least 50% of the microparticles are less than 5 μm, preferably less than 3 μm, the microparticles comprising the antigen(s) entrapped or encapsulated by a biodegradable polymer in combination with (2) antigen(s) presented so as to produce an immune response polarised in favor of a $T_H2$ response. To produce an immune response polarised in favor of a $T_H2$ response, the antigen(s) can be presented as nanoparticles sized such that at least 50% of the nanoparticles are less than 600 nm, preferably less than 500 nm, the nanoparticles comprising the antigen(s) entrapped or encapsulated by a biodegradable polymer; as soluble antigen(s); and/or as antigen(s) adsorbed or presented at least in part on the surface of a particle. The administration of the antigen-containing microparticles in combination with the antigen presented so as to produce an immune response polarised in favor of a $T_H2$ response can be simultaneous, separate, or sequential. A vaccine formulation for parenteral administration comprising antigen entrapped or encapsulated microparticles in combination with antigen presented so as to produce an immune response polarised in favor of a $T_H2$ response such as antigen entrapped or encapsulated nanoparticles is also provided.

The present invention also provides a method of providing protective immunity against *B. pertussis*, comprising parenterally administering to a subject microparticles sized such that at least 50% of the microparticles are less than 5 μm, preferably less than 3 μm, the microparticles comprising at least one *B. pertussis* antigen entrapped or encapsulated by a biodegradable polymer. The present invention also provides a method of providing protective immunity against *B. pertussis*, comprising parenterally administering to a subject nanoparticles sized such that at least 50% of the nanoparticles are less the 600 nm, preferably less than 500 nm, the nanoparticles comprising at least one *B. pertussis* antigen entrapped or encapsulated by a biodegradable polymer. Additionally, the present invention provides a method of providing protective immunity against *B. pertussis*, comprising parenterally administering to a subject microparticles sized such that at least 50% of the microparticles are less than 5 μm, preferably less than 3 μm, the microparticles comprising at least one *B. pertussis* antigen entrapped or encapsulated by a biodegradable polymer in combination with at least one *B. pertussis* antigen presented so as to produce an immune response polarised in favor of a $T_H2$ response, such as at least one *B. pertussis* antigen presented as nanoparticles sized such that at least 50% of the nanoparticles are less than 600 nm, preferably less than 500 nm, the nanoparticles comprising the at least one *B. pertussis* antigen entrapped or encapsulated by a biodegradable polymer; as soluble *B. pertussis* antigen; and/or as *B. pertussis* antigen absorbed or presented at least in part on the surface of a particle.

Preferably, the antigen is capable of eliciting an immune response upon administration, the antigen being entrapped and/or encapsulated within a biocompatible, biodegradable polymer carrier material. Routes for parenteral administration include intraperitoneal (i.p.), subcutaneous (s.c.) and intramuscular (i.m.) routes of administration. Preferably, the method for entrapping and/or encapsulating the antigen within the polymer carrier material is a solvent evaporation based process for formation of antigen entrapped or encapsulated in microparticles or a coacervation based process for formation of antigen entrapped or encapsulated in nanoparticles.

The present invention further relates to a method for the prevention of B. pertussis which method comprises eliciting a $T_H1$ immune response by the administration of a composition comprising inactivated B. pertussis toxin and/or FHA encapsulated in poly (DL-lactide-co-glycolide) microparticles, wherein encapsulation of the inactivated B. pertussis toxin and/or FHA in poly (DL-lactide-co-glycolide) particles is carried out by solvent evaporation and wherein administration is by way of parenteral injection.

Additionally, the present invention further relates to a method for the prevention of B. pertussis which method comprises eliciting a $T_H2$ immune response by the administration of a composition comprising inactivated B. pertussis toxin and/or FHA encapsulated in poly (DL-lactide-co-glycolide) nanoparticles, wherein encapsulation of the inactivated B. pertussis toxin and/or FHA in poly (DL-lactide-co-glycolide) particles is carried out by coacervation and wherein administration is by way of parenteral injection.

BRIEF DESCRIPTION OF THE DRAWINGS

FIG. 2 shows the $T_H1/T_H2$ responses following parenteral immunization with PTd–PLGA microparticles (batch PTd–1 of Example 2) prepared by solvent evaporation. Three groups of mice received a single dose of 5 μg PTd–PLGA, PTd with alum or in solution in PBS. The levels of IFN-γ (see FIG. 2A) and IL-5 9 (see FIG. 2B) were determined by specific immunoassays in cultured spleen cells three days after stimulation with PT. Medium=negative control; iPT=inactivated PT: B. pertussis=active pertussis bacteria and anti-CD/PMA=the positive control anti-CD3 antibody/phorbol 12-myristate-13 acetate;

FIG. 4 shows the serum antibody titres to PTd following i.p. administration as described in Example 7 of PTd+FHA in PLGA (see FIG. 4A) (5 μg each of PTd and FHA entrapped in PLGA microparticles according to Example 2 and 3); PTd+FHA+alum (see FIG. 4B) (5 μg each of Ptd and FHA adsorbed to alum; and PLGA (see FIG. 4C) (i.p.) (empty PLGA microparticles) to balb/c mice;

FIG. 5 compares the $T_H1/T_H2$ responses following parenteral immunization of balb/c mice with PTd+FHA in PLGA (5 μg each of PTd and FHA entrapped in PLGA microparticles according to Example 2 and 3; 4 animals) and PTd+FHA+alum (5 μg each of PTd and FHA adsorbed onto alum; 4 animals). The levels of IFN-γ (see FIGS. 5A and 5B) and IL-5 (see FIGS. 5C and 5D) were determined by specific immunoassays in cultured spleen cells three days after stimulation with PT. iPt=inactivated PT; FHA=filamentous haemagglutinin; B. pertussis=active pertussis bacteria and anti-CD3/PMA=the positive control anti-CD3 antibody/phorbol 12-myristate-13 acetate;

FIG. 6 shows the $T_H1/T_H2$ responses following i.p. administration of low dose (1 μg) FHA encapsulated in PLGA wherein FIG. 6A reflects the levels of γ-IFN, and FIG. 6B reflects the levels of IL-5. Spleen cells from individual mice were stimulated with medium along (O), inactivated PT (PT), filamentous haemagglutinin (FHA), active pertussis bacteria (BP) and the positive control anti-CD3 antibody/phorbol 12-myristate-13 acetate (PMA/CD3);

FIG. 9 shows the $T_H1$ response (IFN-γ) and the $T_H2$ response (IL-5) following i.m. immunization with Treatment F of Example 10. The levels of IFN-γ (see FIG. 9B) and IL-5 (see FIG. 9A) were determined by specific immunoassays in cultured spleen cells from 5 animals (Mouse 1 through Mouse 5) three days after stimulation with PT. BG=negative control; PT-inactivated PT; B. pert=active pertussis bacteria and PMA/aCD3=the positive control anti-CD3 antibody/phorbol 12-myristate-13 acetate; and FIG. 10 shows the $T_H1/T_H2$ responses following parenteral immunization with coacervated nanoparticulate Treatments A–F of Example 11. The levels of IFN-γ (see FIG. 10A) and IL-5 (see FIG. 10B) were determined by specific immunoassays in cultured spleen cells three days after stimulation with PT. iPT–1=activated PT (1.0 μg/ml); iPT–5=inactivated PT (5.0 μg/ml); FHA–5=FHA (5.0 μg/ml); BP=active pertussis bacteria and PMA/CD3=the positive control anti-CD3 antibody/phorbol 12-myristate-13 acetate.

DETAILED DESCRIPTION OF THE INVENTION

Figure 1:
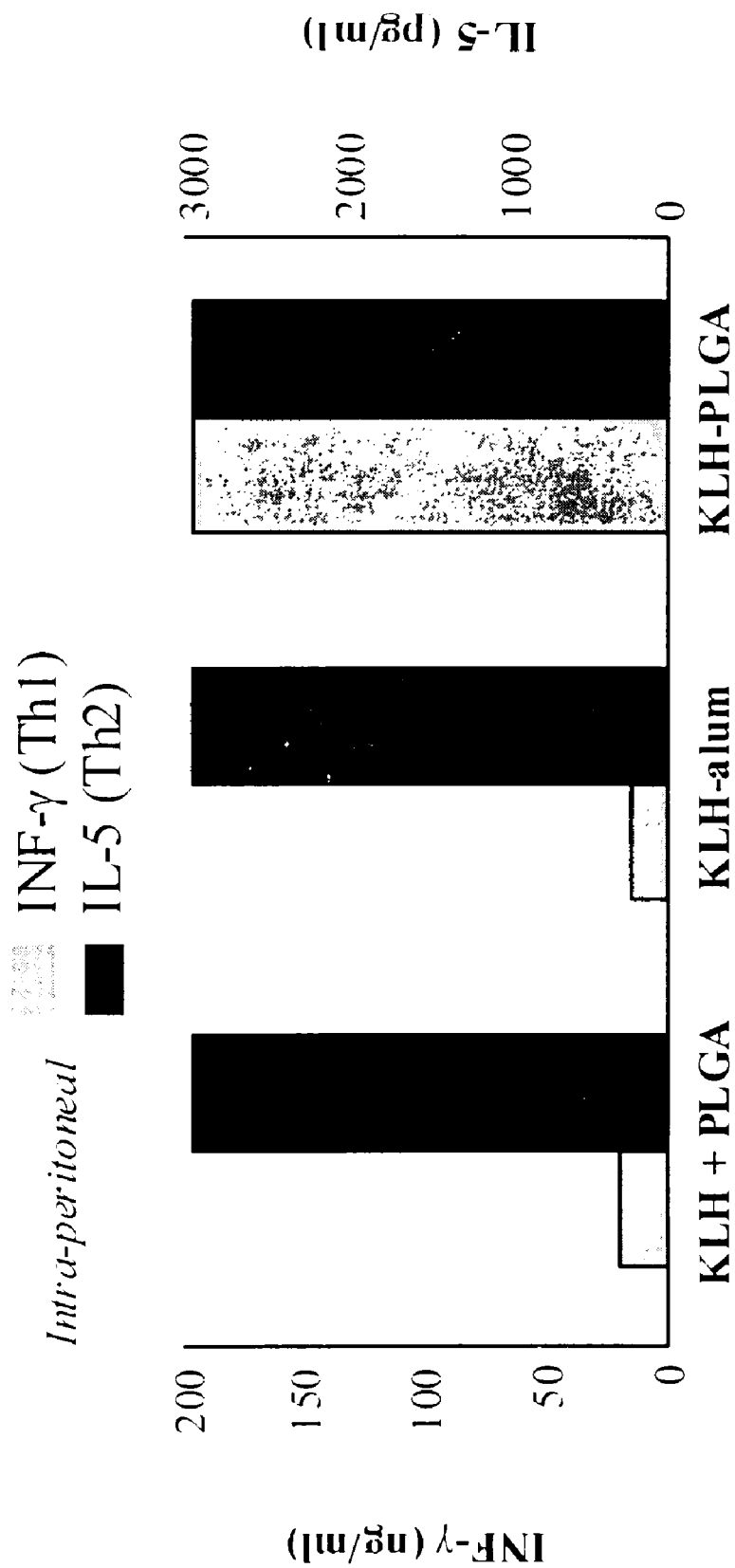
FIG. 1 shows the $T_H1/T_H2$ responses following parenteral immunisation with KLH entrapped in PLGA. Four groups of 4 mice received i.p. inoculation with 5.0 μg of KLH encapsulated in PLGA microparticles (KLH–PLGA), adsorbed to alum (KLH–alum) or in solution combined with empty PLGA microparticles (KLH+PLGA). Mice were immunised twice (0 to 4 weeks) and sacrificed two weeks later. Spleen cells from individual mice were stimulated with 0.03–20 μg/ml of KLH or with medium along. After 3 days culture supernatants were tested for IL-5 IFN-γ by specific immunoassays. Each bar represents the mean response for 4 mice in each group. Note the difference in the scale for IL-5 (pg/ml) and IFN-γ (ng/ml)
Figure 3:
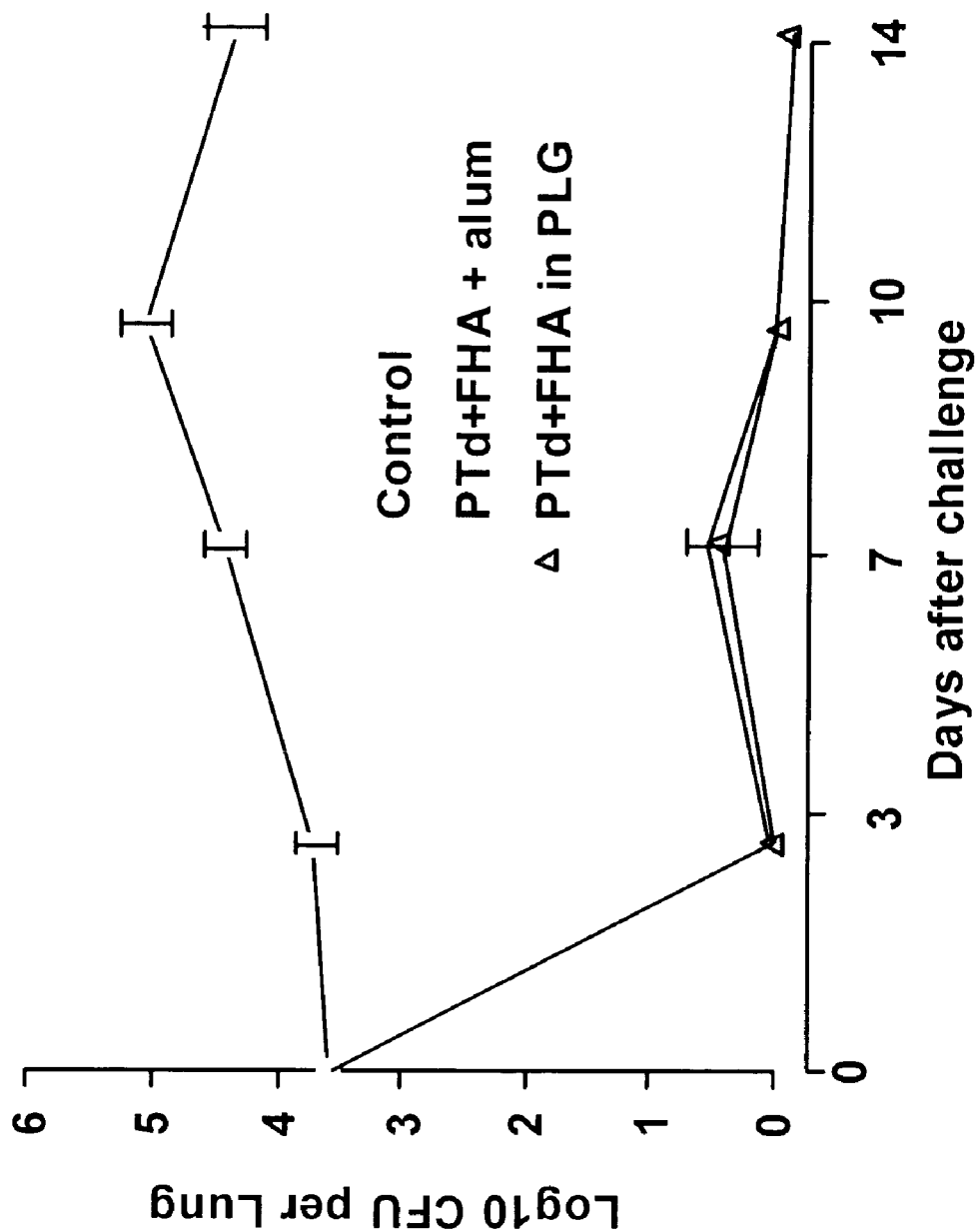
FIG. 3 shows a plot of $Log_{10}$ CFU counts per lung versus Days after challenge for the control group (immunised with empty PLGA microparticles). PTd–FHA–alum group (immunised with 5 μg each of PTd and FHA adsorbed onto alum) and PTd+FHA in PLG group (immunised with 5 μg each of PTd and FHA entrapped in PLGA microparticles according to Examples 2 and 3) for the challenge study in balb/c mice described in Example 7.
Figure 7:
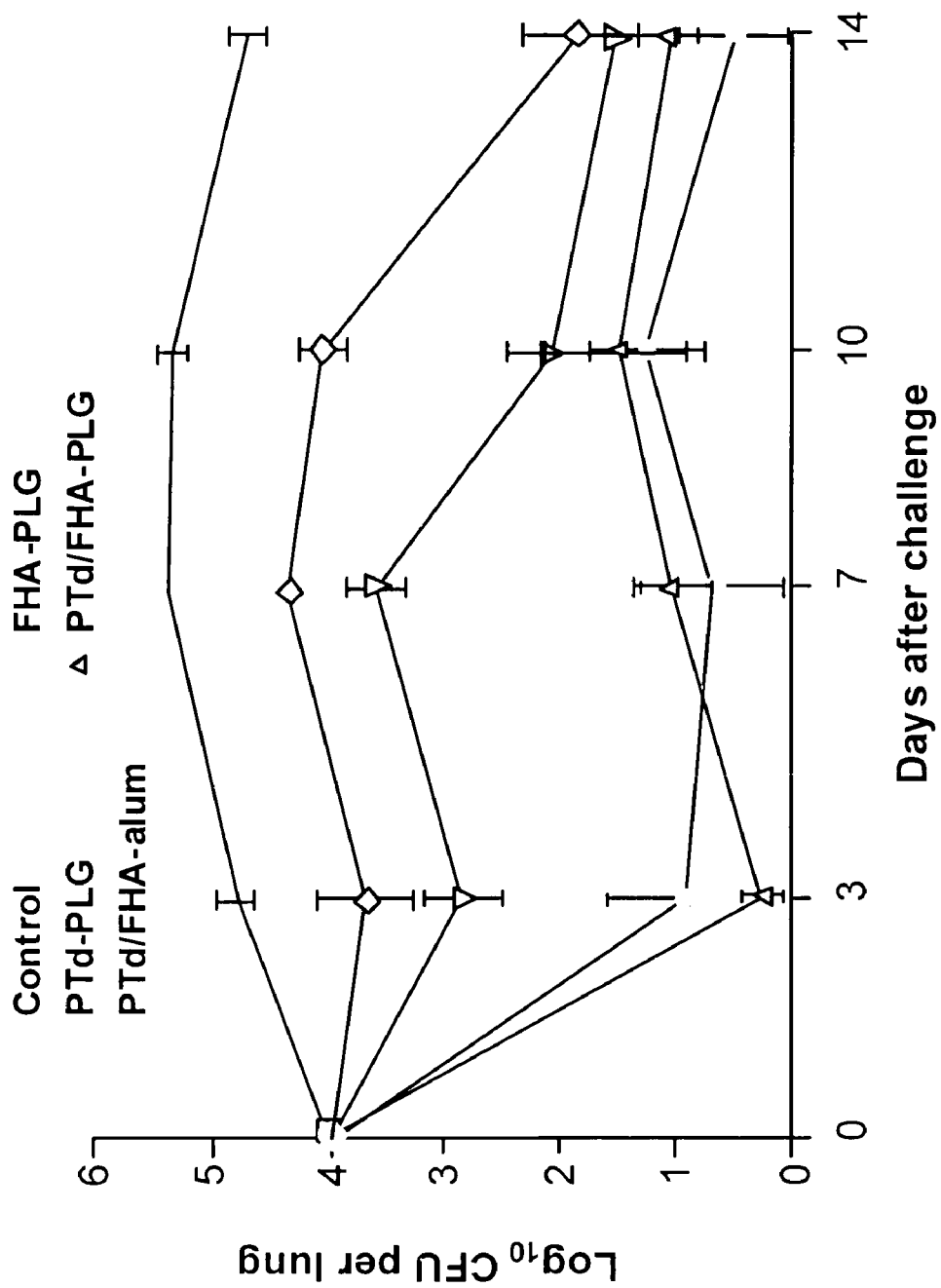
FIG. 7 shows a plot of $Log_{10}$ CFU counts per lung versus Days after challenge for the control group (immunised with empty PLGA microparticles), PTd–PLG group (immunised with 1 μg of PTd entrapped in PLGA microparticles) and PTd/FHA–PLG group (immunised with 1 μg each of PTd and FHA entrapped in PLGA microparticles) for the low dose challenge study in balb/c mice described in Example 8.

While vaccine formulations which comprise antigens loaded onto polymer particles are known in the prior art it has now been found that the choice of biocompatible carrier material, the method of loading of the biologically active agent (i.e., the method for adsorbing and/or encapsulating the biologically active agent onto and/or within the biocompatible, biodegradable polymer material), the size of the particles and/or the route of administration are all contributing factors in determining the nature of the immune response produced. By a suitable combination of the above listed determinants a composition may be prepared which elicits a particular polarised immune response. Polarisation of the immune response may be characterised by determination of the relative proportions of $T_H1$ and $T_H2$ indicators, typically cytokines such as IFN-γ, TNF, IL-2 or IL-12 and IL-5, IL-4, IL-6 or IL-10 specific to $T_H1$ and $T_H2$ responses, respectively.

It has now been found that polarisation of the $T_H1$ immune response over the $T_H2$ immune response can be induced by parenteral administration of appropriately sized antigen-loaded microparticles and that polarisation of the $T_H2$ immune response over the $T_H1$ immune response can be induced by parenteral administration of appropriately sized antigen-loaded nanoparticles. While not wishing to be limited by any theory of the mechanism behind this differentiation, it is possible that the different polarization obtained from administration of antigen entrapped microparticles and antigen entrapped nanoparticles may relate to the physical positioning of the antigen. For instance, some antigen may be presented on the exterior of the nanoparticles compared to relatively more antigen entrapped within the microparticles. Support of a relationship between $T_H2$ polarisation and externally associated antigen can be found from data showing a $T_H2$ polarisation following presentation of soluble antigen, such as that presented in Example 5 below (administration of soluble antigen in combination with empty microparticles).

Preferable routes for parenteral administration include i.p, i.m., and s.c., most preferably i.p. and i.m.

Biologically active agents suitable for the practice of the present invention are typically antigens capable of eliciting a polarised $T_H1$ immune response (e.g., viral antigens, cancer antigens, allergens etc.), a polarized $T_H2$ response (e.g., toxoid antigens, parasite antigens etc.) or a mixed $T_H1/T_H2$ response upon administration. Preferred antigens include those selected from the list comprising of PTd, inactivated *pertussis* toxin or pertactin; FHA, filamentous hemaglutinin; TT, tetanus toxoid; HIV gp-120; hepatitis B surface antigen; DT, diptheria toxoid; HSV, herpes simplex 1; HPV, human papilloma virus; polio; influenza epitope; *H. pylori*; shigella; chlorea; salmonella; rotavirus; RSV, respiratory virus; yellow fever; hepatitis A and C; meningoccoccal types A–C; pneumococcal; parasites such as leischmania; mycobacteria such as tuberculosis; and cancer vaccine antigens As used herein, the term "protective immunity" refers to at least 75% clearance, more preferably 90% clearance of the challenging agent, such as an infectious agent, from the subject preferably within 2 weeks after the introduction of the challenging agent, more preferably within 1 week, most preferably within 3 days.

As used herein, the term "pharmaceutically effective amount" refers to the amount of antigen required to elicit a protective immunity response to that antigen. For instance, in mice, protective immunity is achieved with an amount of a *B. pertussis* antigen(s) in the 1–5 μg range for each antigen given parenterally in multiple doses, such as two doses, or in a single dose.

As used herein, references to the sizes of microparticles and/or nanoparticles refer to sizes as determined by visual assessment of scanning electron micrographs and/or, where indicated, laser light diffractometry.

It has been found that the choice of biocompatible, biodegradable polymer material used as a carrier for entrapping or encapsulating the antigen, the size of the resulting particles and/or the method of loading the carrier with antigen are important in defining the nature of immune response achieved. Preferably the biocompatible, biodegradable polymer material is a copolymer of lactic acid and glycolic acid, such as 50:50 poly (D,L-lactide-co-glycolide), poly (lactide-co-glycolide), and enantiomers thereof or a polymer of lactic acid, such as poly (lactide) and enantiomers thereof. The antigen can be loaded by a solvent evaporation type process, a coacervation process or a spray drying process, preferably by a solvent evaporation type process or a coacervation method. Further details of the loading processes are given in the Examples below.

As will be further appreciated from the examples below the nature of the immune response elicited by antigen loaded polymer particles does not depend on a single factor, but is governed by a combination of a number of factors.

EXAMPLES

All percentages are by weight (w/w) unless other wise stated. The following abbreviation are used throughout the examples: KLH, keyhole limpet hemacyanin; PTd, inactivated *pertussis* toxin; FHA, filamentous hemaglutinin; PLA, poly lactide; PLGA, poly lactide-co-glycolide; DCM, dichloromethane; PVA, poly vinyl alcohol; PBS, phosphate buffer solution.

Example 1

Preparation of KLH–PLGA Microparticles Using a Solvent Evaporation Method

A polymer solution of PLGA [poly (D,L-lactide-co-glycolide), 50:50; i.v.=0.94 dl/g; supplied b Boehringer Ingelheim] in dichloromethane (10% PLGA in 10 ml DCM) was prepared two hours prior to use and subsequently chilled 30 minutes prior to use. The antigen, KLH (supplied by Calbiochem as a powder), was prepared as an aqueous solution (5.1 mg KLH in 1 ml water) containing 2% PVA. A first water-in-oil emulsion was prepared by adding the antigen solution to the polymer solution and homogenising for 1 min. at 24,000 rpm on ice. This first emulsion was poured slowly into an aqueous solution of PVA (40 ml, 3% PVA) forming a second water-oil-water emulsion and homogenisation was continued for 2 min. with a 15 sec. break [1 min.; 15 sec. break; 1 min.]. The resulting emulsion was stirred for 2 hours to evaporate the dichloromethane. The antigen-loaded particles (75% yield) were collected by centrifugation (10,000 rpm for 15 min).

The morphology and the particle size of the KLH–PLGA particles were examined by scanning electron microscopy (SEM) using Leica Cambridge S360. Samples were mounted on stubs, gold coated and scanned at magnifications of ×3,000–10,000. Particle size assessment by SEM was carried out by dividing the micrographs at the 5,000 or 10,000 magnification into different fields and counting the number of particles greater and less than 3 microns and 5 microns (1 micron=$10^{-6}$ m=1 μm). Particle size determination was also carried out by laser diffractometry using a Malvern Mastersizer S Ver.2.14. The microparticles were suspended in filtered 0.1% TWEEN 20, sonicated for 5 minutes and analysed with continuous stirring. KLH–PLGA particles prepared as detailed above were found to have a smooth spherical appearance and a D50% of 2.5 μm by laser light diffraction. By SEM, it could be seen that at least 50% of the particles had a diameter less than 5 microns.

The loading of microparticles with antigen was determined by digesting 10 mg of loaded microparticles in 3 ml of 5% SDS/0.1 M NaOH for up to 60 hours with continuous shaking at room temperature. The particles were completely digested during this period. The pH of the solution was adjusted to pH 11.2 with 0.1 M HCl and protein content was determined using a Bicinchoninic acid (BCA) protein assay kit. Equivalent control particles containing no antigen were also digested. The loading was calculated as follows:

$$\text{Actual loading } (\mu g/mg) = \frac{\text{concentration in sample } (\mu g/ml) \times \text{total volume digested (ml)}}{\text{weight of particles (mg)}}$$

$$\% \text{ entrapment efficiency} = \frac{\text{actual loading } (\mu g/mg) \times 100}{\text{theoretical loading } (\mu g/mg)}$$

where the theoretical loading is calculated from the amount of antigen added to the formulation divided by the amount of polymer used.

KLH–PLGA particles prepared according to the present example were found to have a loading of 3.1 μg antigen/mg particles, giving an entrapment efficiency of 94%.

The in vitro release of antigen from the loaded particles was determined as follows: antigen loaded microparticles and control microparticles (prepared in a similar manner, but containing no antigen) were accurately weighed and dispersed in PBS containing 0.02% sodium azide as a bacteriostatic agent. Samples were immersed in a water bath at 37° C. and shaken continuously. At appropriate time intervals, 2.2 ml aliquots were removed with a syringe, filtered and the protein content measured in duplicate by BCA assay. KLH–PLGA particles prepared according to the present example were found to release 80% of loaded antigen after 1 hour and 100% of loaded antigen after 24 hours.

The procedure detailed above was repeated to form a second batch of KLH–PLGA microparticles. This second batch of microparticles appeared smooth and spherical under SEM with at least 50% of the particles less than 5 microns, the D50% was determined to be 2.2 μm; the loading was found to be 3.5 μg/mg representing 94% entrapment efficiency; and 76% of the antigen was determined to be released after 1 hour, with 90% being released after 24 hours.

Antigen loaded microparticles obtained from these two batches were pooled together for an immunogenicity study in mice as discussed in Example 5 below.

Example 2

Preparation of PTd–PLGA Microparticles Using a Solvent Evaporation Method

Using a method substantially the same as that described in Example 1 above, PTd (supplied by Katetsuken) loaded PLGA particles were prepared. The polymer solution was 6.7% PLGA in 15 ml DCM and the antigen solution was 744 μg PTd in 2 ml water containing 0.9% PVA. The first water-in-oil emulsion was poured into 80 ml aqueous PVA (3% PVA) to form the water-oil-water emulsion. The emulsion was left over night to evaporate the DCM. After collection (88% yield), the microparticles were washed with chilled autoclaved water (30 ml).

Characterisation of these particles, identified as PTd–1 in Table 1 below, showed that the microparticles formed were smooth and spherical in appearance with at least 50% of the particles less than 5 microns in diameter. Laser light diffractometry showed that the particles had a D50% of 2.5 μm. The microparticles were loaded with antigen at 0.12 μg/mg, representing an entrapment efficiency of 15%.

The in vitro release of PTd loaded microparticles was determined according to the following method: 30 mg of microparticles were dispersed in PBS (4.0 ml) containing 0.02% sodium azide. The sample was placed in a water bath at 37° C. and shaken continuously. At appropriate time intervals the sample was removed from the water bath and centrifuged to pellet the particles. The supernatant was removed and the protein content was determined in duplicate. Three ml of fresh PBS was added to the microparticles to maintain sink conditions and the incubation was continued. PTd–PLGA particles prepared according to the present example (PTd–1) were found to release 22% of loaded antigen after 1 hour and 56% of loaded antigen after 24 hours followed by biphasic release over 20 days.

Additional batches of PTd–PLGA microparticles were made following substantially the same procedure as given above using quantities of the various components as summarised in Table 1 below. In batches PTd–2 through PTd–6, no PVA was added to the initial antigen solution and 40 ml chilled autoclaved water was used to wash the recovered microparticles. In each case the resulting antigen loaded microparticles were found to be smooth and spherical in appearance with at least 50% of the particles less than 5 microns in diameter.

TABLE 1

| Batch No. | PTd (μg) | Aq. Vol (ml) | % PLGA | DCM (ml) | 3% PVA (ml) | Load (μg/mg) | % EE | D50% (μm) | 1 hr (%) | 24 hr (%) |
|---|---|---|---|---|---|---|---|---|---|---|
| PTd-1 | 744 | 2 | 6.7 | 15 | 80 | 0.12 | 15 | 2.5 | 22 | 56 |
| PTd-2 | 1536 | 1.0 | 4 | 10 | 40 | 1.2 | 31 | 3.0 | 30 | |
| PTd-3 | 2760 | 1.5 | 4 | 20 | 80 | 1.3 | 33 | 3.3 | * | * |
| PTd-4 | 3130 | 1.5 | 4 | 20 | 80 | 1.3 | 34 | 2.4 | * | * |
| PTd-5 | 2140 | 2.0 | 4 | 20 | 80 | 1.1 | 42 | 3.2 | * | * |
| PTd-6* | — | — | — | — | — | — | — | — | 17 | 21 |

3% PVA is the volume of PVA solution to which the antigen PLGA water-in-oil emulsion is added;
Load is the antigen loading of the microparticles;
% EE is the % entrapment efficiency;
D50% is the average diameter of the microparticles;
1 hr is the antigen released after 1 hour;
24 hr is the antigen released after 24 hrs.
*The loaded microparticles obtained from PTd-3, PTd-4 and PTd-5 were pooled for antigen release assay and i.p. protection study (see Example 7 below).

Example 3

Preparation of FHA-PLGA Microparticles Using a Solvent Evaporation Method

A procedure substantially similar to that used in Example 2 was employed for the preparation of FHA-loaded PLGA microparticles. Two batches of FHA-PLGA microparticles were prepared. For these two batches (FHA-1 and FHA-2 in Table 2 below) the polymer solution was 4% PLGA in 20 ml DCM and the antigen solution was 0.87 µg FHA in 2 ml water containing no PVA. The first water-in-oil emulsion was poured into 80 ml aqueous PVA (3% PVA) to form the water-oil-water emulsion. The characteristics of these two batches are given in Table 2 below. FHA-1 and FHA-2 were pooled (the pooled microparticles are labelled FHA-3 in Table 2) for antigen release determination and i.p. protection studies (see Example 7 below). SEM analysis showed the FHA-1 and FHA-2 microparticles to be smooth and spherical in nature with at least 50% of the particles less than 5 microns in diameter.

TABLE 2

| Example No. | Loading (mg/mg) | % EE | D50% (µm) | 1 hr (%) | 24 hr (%) |
|---|---|---|---|---|---|
| FHA-1 | 0.94 | 87 | 3.0 | * | * |
| FHA-2 | 1.09 | 100 | 4.3 | * | * |
| FHA-3* | — | — | — | 25 | 49 |

Example 4

Preparation of Antigen Entrapped or Encapsulated Nanoparticles

An aqueous solution (A) of a polymer, surface active agent, surface stabilising or modifying agent or salt, or surfactant preferably a polyvinyl alcohol (PVA) or derivative with a% hydrolysis 50–100% and a molecular weight range 500–500,000, most preferably 80–100% hydrolysis and 10,000–150,000 molecular weight, is introduced into a vessel. The mixture (A) is stirred under low shear conditions at 10–2000 rpm, preferably 100–600 rpm. The pH and/or ionic strength of this solution may be modified using salts, buffers or other modifying agents. The viscosity of this solution may be modified using polymers, salts, or other viscosity enhancing or modifying agents.

A polymer, preferably poly(lactide-co-glycolide), polylactide, polyglycolide or a combination thereof or in any enantiomeric form is dissolved in water miscible organic solvents to form organic phase (B). Most preferably, a combination of acetone and ethanol is used in a range of ratios from 0:100 acetone; ethanol to 100:0 acetone: ethanol depending upon the polymer used. Additional polymer(s), peptide(s) sugars, salts, natural/biological polymers or other agents may also be added to the organic phase (B) to modify the physical and chemical properties of the resultant particle product.

An antigen or bioactive substance may be introduced into either the aqueous phase (A) or the organic phase (B). The organic phase (B) is added into the stirred aqueous phase (A) at a continuous rate. The solvent is evaporated, preferably by a rise in temperature over ambient and/or the use of a vacuum pump. The particles are now present as a suspension (C).

The particles (D) are then separated from the suspension (C) using standard colloidal separation techniques, preferably by centrifugation at high 'g' force, filtration, gel permeation chromatography, affinity chromatography or charge separation techniques. The supernatant is discarded and the particles (D) re-suspended in a washing solution (E) preferably water, salt solution, buffer or organic solvent(s). The particles (D) are separated from the washing liquid in a similar manner as previously described and re-washed, commonly twice.

The particles may then be dried. Particles may then be further processed for example, tabletted, encapsulated or spray dried.

The release profile of the particles formed above may be varied from immediate to controlled or delayed release dependent upon the formulation used and/or desired.

Antigen loading may be in the range 0–90% w/w.

Specific examples include the following:

A PTd (168 µg/ml) or FHA (264 µg/ml) solution was first dispersed in a PVA (mwt=13000–23000; 98% hydrolysis) solution while stirring at 400 rpm with the temperature set at 25° C. A polymer solution (prepared by dissolving PLGA; 50:50; either RG504 or RG504H supplied by Boehringer Ingelheim into the organic phase) was added slowly into the aqueous phase to form coacervates that hardened following evaporation of the organic solvent. The nanoparticles were then recovered by centrifugation at 15,000 rpm for 30 minutes and washed three times with autoclaved deionised water. The wet pellet was allowed to dry at ambient temperature under a vacuum. Batches having a theoretical loading of 0.3% PTd (RG504H and RG504 polymer), 0.2% FHA (RG504H and RG504 polymer) were prepared according to Table 3.

TABLE 3

| Batch | 5% w/v PVA soln. | PLGA polymer (g) | Acetone (ml) | Ethanol (ml) | antigen (ml) |
|---|---|---|---|---|---|
| 0.3% PTd | 546.4 | 2.991 | 67.5 | 7.5 | 53.6 |
| 0.2% FHA | 577.3 | 2.994 | 67.5 | 7.5 | 22.7 |

Scanning microscopy was employed to assess the nanoparticle morphology and size. The nanoparticles were mounted onto SEM stubs, sputter coated using an Emitech K550 sputter coater set at 25 mA for 3 minutes and scanned using a Leica Cambridge S360. Micrographs were taken at magnifications of 500–20,000×. Particle size assessment by SEM was carried out by dividing the micrographs at the 15,000 magnification into different fields and counting the number of particles greater and less than 600 nm and 500 nm. The SEM analysis showed that for both the PTd-PLGA and FHA-PLGA nanoparticles were approximately spherical in shape with smooth surfaces. At least 50% of the particles were less than 600 nm at the 15 k magnification, although there was some evidence of aggregation.

Antigen loading was determined by measuring the total protein content of the nanoparticles using a BCA protein assay as described in Example 1. The nanoparticles prepared according to the present example were found to have the potencies and encapsulation efficiencies as given in Table 5.

TABLE 4

| Batch | Potency (μg/ml) | Encapsulation efficiency (%) |
|---|---|---|
| 0.3% PTd-RG504H | 1.3 | 43.3 |
| 0.2% FHA-RG504H | 0.9 | 45.0 |
| 0.3% PTd-RG504 | 1.3 | 43.3 |
| 0.2% FHA-RG504 | 1.0 | 50.0 |

The in vitro release of antigen from the loaded particles was determined by suspending 50 mg of nanoparticles in 10 ml PBS, pH 7.4, containing 0.02% w/v sodium azide in glass tubes and incubating at 37° C. At predetermined time intervals, a 3 ml sample was removed and the total protein released was determined by the BCA protein assay described above. PTd–PLGA formulations showed a large burst effect of approximately 45% in the first hour followed by a very gradual release up to 55% at 24 hours. In comparison, FHA–PLGA formulations showed a much lower burst release of 14% at 1 hours up to 18% after 24 hours.

Example 5

Immune Response Upon i.p. Administration of KLH–PLGA Microparticles to balb/c Mice The immunogenicity of KLH entrapped in biodegradable microparticles was assessed in mice following parenteral (i.p.) administration and compared with the same antigen in solution (phosphate buffered saline: PBS) or adsorbed to alum. Further control groups included KLH in solution with empty PLGA microparticles, empty PLGA microparticles alone or PBS alone. Microparticles from the two batches of Example 1 were pooled and suspended in PBS at a concentration equivalent to 100 μg of antigen per ml or diluted accordingly for lower doses. Each mouse was immunised with 0.3 ml once or twice at a four week interval and immune responses were assessed 2 weeks after the last immunisation.

Serum and mucosal secretions (lung homogenates) were tested for anti-KLH IgG and IgA antibody levels by ELISA. Systemic cellular immune responses were assessed using spleen from immunised mice. The spleen cells from 4 to 6 individual mice in each experimental group were cultured in triplicate wells of duplicate 96-well microtitre plates with a range of concentrations of antigen (0.16 to 100 μg/ml). The mitogens Concanavlin A or PMA and anti-CD3-antibody or medium along were included as positive and negative controls respectively. After 24 and 72 hours supernatants were removed from one plate and stored at −70° C. for cytokine analysis. The levels of interferon γ (IFN-γ) and interleukin-5 (IL-5) were determined by immunoassay as quantifiable markers of induction of antigen-specific $T_H1$ and $T_H2$ subpopulations respectively. Additionally, the proliferation of T cell cultures were assessed in four day cultures, by [$^3$H]-thymidine incorporation.

A single i.p. immunisation with 20 μg KLH entrapped in PLGA microparticles induced potent cellular immune responses with high nanogram levels of IFN-γ produced by spleen cells following in vitro stimulation with KLH over a wide dose range. Picogram levels of IL-5 were also detected in antigen-stimulated spleen cell supernatants but the levels were comparatively lower than that observed with spleen cells from animals immunised with KLH adsorbed to alum. Overall the responses were polarised to $T_H2$ with antigen adsorbed onto alum and to $T_H1$ with microencapsulated antigen. FIG. 1 shows the immune response following the second immunisation at four weeks. The levels of IL-5 for the microencapsulated KLH were comparable with those observed with alum, but the production of IFN-γ was significantly higher. Furthermore, potent antigen-specific proliferation was observed in spleen cells from mice immunised with KLH entrapped in PLGA microparticles. The stimulation indices (derived by dividing the response to antigen by the response to medium alone) were significantly higher than those observed with spleen cells from mice immunised with KLH adsorbed to alum at all antigen doses tested in vitro.

Following parenteral immunisation with microencapsulated KLH, the levels of KLH-specific IgG in serum were significantly higher than those generated with the soluble antigen and were equal to or greater than that induced with alum absorbed antigen. Co-injection with empty PLGA also appeared to significantly boost the antibody responses to soluble antigen. Although each of the animals immunised with 20 μg of soluble KLH by the i.p. route generated detectable antibody response, the titres were more than 10 fold higher when the antigen was combined with empty PLGA microparticles prior to immunisation. These findings suggest that the $T_H2$ and antibody, but not the $T_H1$ response was significantly boosted following co-injection of empty microparticles with soluble antigen, whereas $T_H1$ responses are enhanced with the microencapsulated antigen.

These results demonstrate that the entrapment of soluble antigen KLH in PLG microparticles significantly enhanced T cell proliferative responses over that observed with soluble antigen and was comparable to that observed with alum adsorbed antigen by the i.p. route. Moreover, encapsulation of the antigen in PLGA appears to favour the induction of $T_H1$ cells.

Example 6

Immune Response Upon i.p. Administration of PTd–PLGA Microparticles to balb/c Mice Similarly to the immunisation regimen of Example 5, batch PTd-1 of Example 2 was used in a preliminary parenteral immunisation study in which mice were immunised with two i.p. inoculations of 5 μg PTd entrapped in PLGA microparticles, adsorbed to alum or in solution combined with empty PLGA microparticles. Control mice were immunised with PBS alone or with empty PLGA microparticles alone. Antibody responses were detected by ELISA two weeks after administration of the second dose. Potent anti PTd–IgG titres were observed after each of the two immunisations, with PTd–PLGA titres on the order of $1 \times 10^6$, comparable to those obtained with alum, being obtained after the second immunisation. No responses were seen in mice exposed to empty PLGA microparticles. Surprisingly, PTd in solution gave responses in 3/5 mice; these responses are unlikely to be sustained over time compared to PTd–PLGA or PTd–alum and they were not seen in the first immunisation. The effects of PTd in solution were enhanced in the presence of empty PLGA.

FIG. 2 shows the cytokine analysis after first i.p. immunisation, demonstrating a dominant $T_H1$ cell-mediated immune response to PTd–PLG. Upon re-exposure to *pertussis*, a high level of IFN-γ ($T_H1$) and only modest levels of IL-5 ($T_H2$) were seen in the spleen cell cultures form animals previously immunised with PTd–PLGA. Cells re-exposed to *pertussis* following a PTd–alum immunisation gave relatively strong IFN-γ and IL-5 production.

Example 7

Pertussis Challenge Study Following i.p. Immunisation of balb/c Mice with the Antigen Combination PTd+FHA

Groups of 20 balb/c mice were immunised i.p. with 5 µg each of PTd and FHA entrapped in PLGA microparticles (using PTd–6 of Example 2 and FHA–3 of Example 3) or adsorbed to alum. The control group received empty PLGA microparticles. The ability of PLGA-entrapped antigen to protect against B. pertussis was examined in a respiratory challenge model. Briefly, following two doses of antigen, four weeks apart, a respiratory B. pertussis infection was initiated in 16 mice per experimental group by aerosol challenge of approximately $2 \times 10^{10}$ cfu/ml (approximately $10^4$–$10^5$ cfu per mouse lung) two weeks after the second immunisation. The mice were sacrificed at different time points over a two-week period and lung homogenates were cultured and examined after 5 days culture for the number of colony forming units (CFU). Four mice from each group were sacrificed prior to challenge to test immune responses on the day of challenge.

The results from the CFU counts 2 hours and 3, 7, 10 and 14 days after challenge, which are shown in FIG. 3, reveal a high level of protection with both PLGA microparticle entrapped and alum adsorbed antigens. These treatments provided clearance of *B. pertussis* by the third day post challenge following challenge 6 weeks after immunisation. The potency index which compares the counts for the test "vaccine" with the un-immunised control group were 88.8 and 88.4 for the PTd+FHA in PLGA and PTd+FHA adsorbed to alum respectively. These potency indices equal or exceed the levels of potency for commercial acellular vaccines, including 3 and 5 component vaccines.

The immune responses on the day of challenge revealed very strong anti-PT antibody responses with the PLG entrapped antigens as shown in FIG. 4. The end point titres were $\log_{10}$ 5.8 for the PLGA group and 5.0 for the alum group. The anti-FHA antibody titres were of the order of 5.0 for both alum and PLGA groups.

Results of the CMI studies revealed positive T cell proliferative responses against inactivated PT and FHA in all mice immunised with PTd and FHA microencapsulated in PLGA or adsorbed to alum. The T cell responses against PT were stronger in the PLGA group, whereas the responses to FHA were stronger in the alum group. FIG. 5 shows the corresponding cytokine analysis from splenic T cells following parenteral immunisation with 5 μg each of PTd and FHA entrapped in PLGA microparticles ($T_H1$ polarisation) and 5 μg each of PTd and FHA adsorbed onto alum (mixed $T_H1/T_H2$ responses). These results confirm that as in the case of KLH entrapped in PLGA, PTd entrapped in PLGA and FHA entrapped in PLGA, entrapment of PTd and FHA together in PLGA polarises the immune response towards $T_H1$ after i.p. delivery. In the case of alum. a mucosal or exclusive $T_H2$ result is found.

Example 8

*Pertussis* Challenge Study Following i.p. Immunisation of balb/c Mice with the Antigen Combination PTd+FHA (Reduced Dose)

Groups of 20 balb/c mice were immunised parenterally (i.p.) at week 0 and at week 4 with 1 μg each of PTd and FHA entrapped in PLGA microparticles: 1 μg each of PTd and FHA adsorbed to alum: 1 μg of PTd entrapped in PLGA microparticles or 1 μg FHA entrapped in PLGA microparticles. The control group received empty PLGA microparticles. The ability of PLGA-entrapped antigen (low dose) to protect against *B. pertussis* was examined in the respiratory challenge model as described in Example 7. The mice were sacrificed at different time points over a two-week period after the aerosol challenge and lung homogenates were cultured and examined after 5 days cultures for the number of colony forming units (CFU). Four mice from each group were sacrificed prior to challenge to test immune responses on the day of challenge.

The results from the CFU counts 2 hours and 3, 7, 10 and 14 days after challenge reveal a high level of protection with 1 μg of FHA and PTd either microencapsulated in PLGA or adsorbed to alum as shown in FIG. 7. Both of these treatments provide substantial clearance of *B. pertussis* by the third day post challenge following challenge 6 weeks after immunisation.

The cytokine data demonstrates significant polarisation to $T_H1$ for the groups treated with FHA and PTd entrapped in PLGA, with PTd entrapped in PLGA and with FHA entrapped in PLGA while a mixed $T_H1/T_H2$ response if seen for the group treated with FHA and PTd adsorbed to alum. FIG. 6 shows the cytokine analysis for FHA entrapped in PLGA microparticles, demonstrating the $T_H1$ polarisation of this formulation. The control group produced little response in the T cells.

ELISA antibody titres for the mice in the five treatment groups were evaluated 2 weeks after the second immunisation, which occurred at week 4. Table 3 presents the mean (SD) serum IgG titres for each group of 4 mice. The results show that the anti-PT antibody titres are not significantly different between the different groups that received formulations that included PTd. However, the anti-FHA antibody levels are significantly stronger in the mice that received alum adsorbed antigens. The levels were about 10 fold lower in the mice that received FHA entrapped in PLGA or FHA and PLGA entrapped in PLGA microparticles.

TABLE 5

| Immunogen | Anti-PT | Anti-FHA |
|---|---|---|
| PTd-PLGA | 5.05 (0.48) | <1.00 |
| PTd/FHA-PLGA | 4.97 (0.32) | 4.54 (0.89) |
| PTd/FHA-alum | 5.20 (0.24) | 5.44 (0.16) |
| FHA-PLGA | <1.00 | 4.47 (0.94) |
| Empty-PLGA | <1.00 | <1.00 |

Example 9

*Pertussis* Challenge Study Following i.p. Immunisation of balb/c Mice with the Antigen Combination PTd+FHA (Delayed Challenge)

Three groups of 20 balb/c mice were immunised parenterally (i.p.) at week 0 and at week 4 with 5 μg each of PTd and FHA entrapped in PLGA microparticles and 5 μg each of PTd and FHA adsorbed to alum and a control group (empty PLGA microparticles). The ability of PLGA-entrapped antigen to protect against *B. pertussis* was examined in the respiratory challenge model. Following two doses of antigen, four weeks apart, a respiratory *B. pertussis* infection was initiated in 16 mice per experimental group by aerosol challenge at week 12. The mice were sacrificed at different time points over a two-week period after the aerosol challenge and lung homogenates were cultured and examined after 5 days culture for the number of colony forming units (CFU). Four mice from each group were sacrificed prior to challenge to test immune responses on the day of challenge.

The results of the cytokine analysis at the 12 week time point are consistent with those reported above for analysis at the 6 week time point, showing a polarisation of the T cell response to type 1 with PTd and FHA entrapped in microparticles and to type 2 with alum adsorbed antigens. Overall, these results reveal persistence, and perhaps even further polarisation, of the $T_H1$ response after immunisation with antigen entrapped in PLGA microparticles versus alum.

Figure 8:
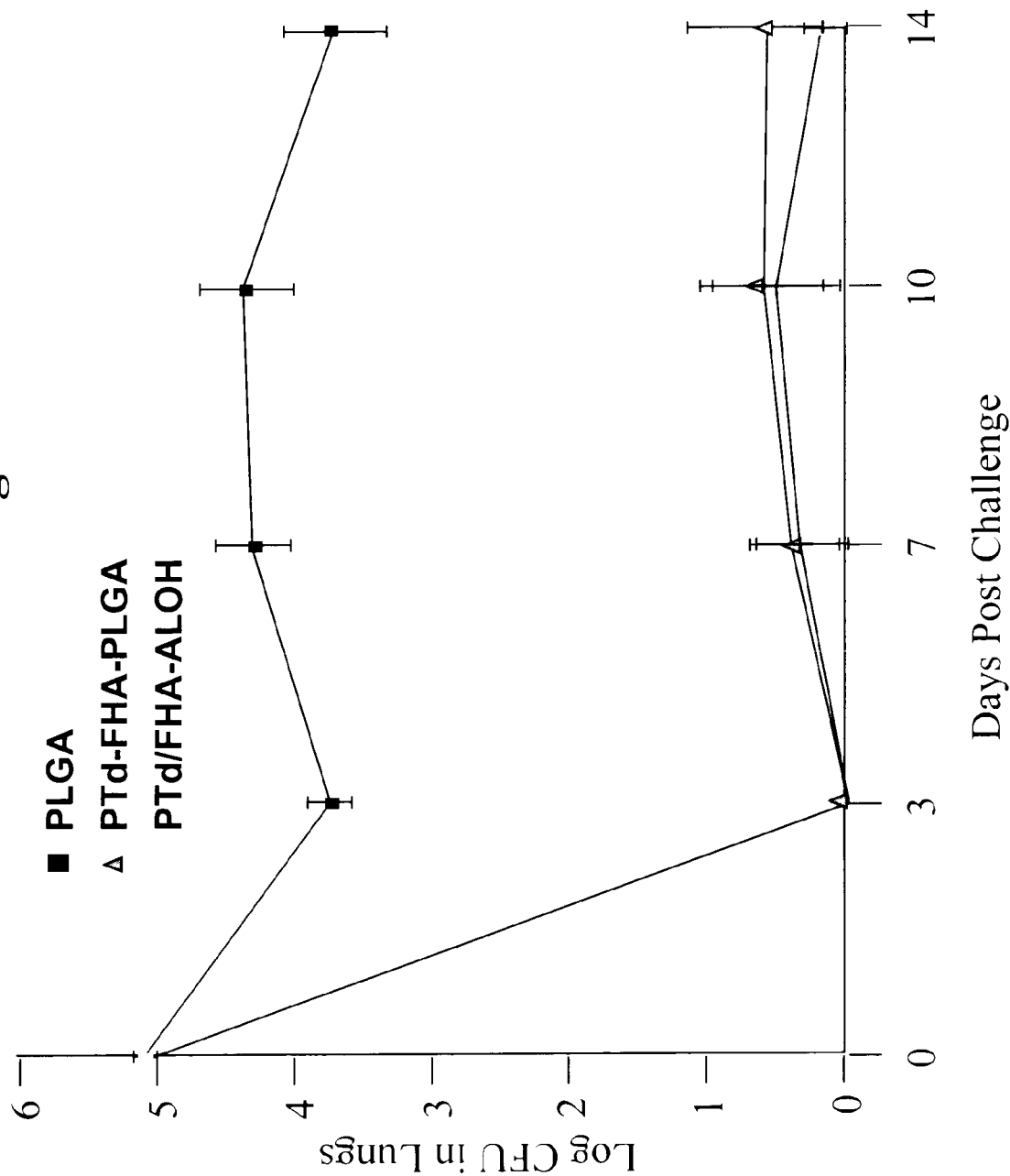
FIG. 8 shows a plot of $Log_{10}$ CFU counts per lung versus days post challenge for the control group (immunised with empty PLGA microparticles). PTd/FHA–alum group (immunised with 5 μg each of PTd and FHA adsorbed onto alum), and PTd/FHA–PLG group (immunised with 5 μg each of PTd and FHA entrapped in PLGA microparticles) for the delayed challenge study in balb/c mice described in Example 9.

As shown in FIG. 8, the results from the CFU counts 2 hours and 3, 7, 10 and 14 days after challenge reveal a high level of protection with 5 μg of FHA and PTd either microencapsulated in PLGA or adsorbed to alum. Both of these treatments provide clearance of *B. pertussis* by the third day post challenge following challenge 12 weeks after immunisation.

Example 10

Immune Response Upon Parenteral Administration (i.p., s.c., i.m.) of PTd–PLGA and FHA–PLGA Microparticles to balb/c Mice Seven groups of 5 balb/c mice were immunized by three different parenteral routes at week 0 and at week 4 with 1 μg each of PTd and FHA in either saline solution or entrapped in PLGA microparticles manufactured similarly to those of Examples 2 and 3 (PTd loading=1.42 μg/mg; FHA loading=1.22 μg/mg; 1.52 mg particles per dose) as follows:

| | |
|---|---|
| Treatment A: | PTd + FHA in solution intraperitoneal (ip.) |
| Treatment B: | PTd + FHA in solution subcutaneous (s.c.) |
| Treatment C: | PTd + FHA in solution intramuscular (i.m.) |
| Treatment D: | PTd + FHA entrapped in PLGA intraperitoneal (i.p.) |
| Treatment E: | PTd + FHA entrapped in PLGA subcutaneous (s.c.) |
| Treatment F: | PTd + FHA entrapped in PLGA intramuscular (i.m.) |
| Treatment E: | Saline only (control) |

The i.p. immunisations were administered in 0.3 ml, the s.c. immunisations (on the back) in 0.2 ml and the i.m. immunisation at two sites in 0.1 ml.

Immune response to these treatments were assessed two weeks subsequent to the second immunisation at week 6. Individual spleen cell preparations from mice per experimental group were tested for antigen-induced proliferation and cytokine production. Serum samples (week 6) from individual mice were assessed over an 8-fold dilution range for anti-PT and anti-FHA IgG.

Analysis of the serum IgG responses revealed clear effects due to the route of administration on the antibody titres, with striking differences between soluble and PLGA entrapped antigen. The s.c. route generated slightly weaker anti-PT antibody response with both soluble and PLGA entrapped antigens (end-point log titres of ~3.5 and 3.7, respectively). The anti-FHA titres were also lowest when soluble and PLGA-entrapped antigens were given by the s.c. route (end-point log titres of 1.8 and 0.4, respectively). However, very strong anti-PT and anti-FHA responses induced with the PLGA microparticle entrapped antigens were observed after i.p. immunisation (end-point log titres of ~4.5 and 2.7, respectively). In contrast, immunisation by the i.m. route induced the strongest IgG responses with the antigens in solution (end-point anti-PT and anti-FHA log titres were 4.3 and 3.8 for i.m. solution).

Overall, the anti-PT responses were strongest with the PLGA entrapped antigens by the i.p. route, whereas the strongest anti-FHA responses were observed with antigens in solution by the i.m. route. These results are consistent with the increased immunogenicity of particulate antigens in the peritoneal cavity, a site rich in phagocytic APC and the slower clearance of soluble antigen administered by the i.m. route.

T cell proliferative responses against inactivated PT and FHA shows that the strongest responses are observed in mice that received microencapsulated or soluble PTd and FHA by the s.c. routes.

Analysis of the cytokine production from spleen cells showed that all of the immunogens induced potent antigen-specific T cell responses but also revealed striking differences between administration of antigens entrapped in PLGA or in solution by different parenteral routes. Overall, the antigens entrapped in PLGA induced a T cell response which was polarised to the $T_H1$ subtype following any route of parenteral immunisation, whereas the response was more polarised to $T_H2$ with the antigen in solution.

The best T cell priming with the soluble antigens was observed with the i.m. route followed by s.c., with the poorest results observed for the i.p. route, especially for IL-5 producing cells. Potent $T_H2$ cytokine production was induced with the soluble antigens given by the i.m. route; the levels of FHA-induced IL-5 exceed 2000 pg/ml for spleen cells in 4 of 5 mice. In contrast, as shown in FIG. 9 for i.m. administration, analysis of the cytokine production following parenteral administration of PLGA microencapsulated antigen to mice revealed that the i.m. route induced IFN-γ production by each of the mice in response to each of the antigen preparations tested whereas IL-5 production was weak or undetectable. This was exactly the pattern seen for the i.p. route as described in FIGS. 1, 5 and 6. However, the responses were less polarised to $T_H1$ with PLGA microencapsulated antigens administered by the s.c. route; the IFN-γ levels were lower and more inconsistent and significant IL-5 responses were detected in 3 of 5 mice. The finding that the i.m. route results in potent $T_H2$ priming with soluble antigen but $T_H1$ priming with PLGA entrapped antigen is new and highly significant.

Similarly to the immunisation regimen given above, a repeat of the above parenteral route study was undertaken in which groups of balb/c mice were immunized at week 0 and week 4 with inoculations of 1 μg of each of the antigens according to the following treatments:

| | |
|---|---|
| Treatment 1: | PTd + FHA in solution subcutaneous (s.c.) |
| Treatment 2: | PTd + FHA in solution intramuscular (i.m.) |
| Treatment 3: | PTd + FHA entrapped in PLGA subcutaneous (s.c.) |
| Treatment 4: | PTd + FHA entrapped in PLGA intramuscular (i.m.) |
| Treatment 5: | empty PLGA subcutaneous (s.c.) (control) |

The ability of these s.c. and i.m. treatments to protect against *B. pertussis* was examined in the respiratory challenge model as described in Example 7. The results from the CFU counts reveal a high level of protection from Treatments 3 and 4 (microparticles injected s.c. and i.m.). Both of these treatments, as well as that of Treatment 2 (antigens in solution, i.m.), provide substantial clearance of *B. pertussis* by the third day post challenge following challenge 2 weeks after the second immunisation. In contrast, neither Treatment 5 (empty PLGA, s.c.) or Treatment 1 (antigens in solution, s.c.) show clearance at the third day post challenge.

Example 11

Immune Response Upon Parenteral Administration of PTd–PLGA and FHA–PLGA Nanoparticles to balb/c Mice The immunogenicity of coacervate formulations of PTd, FHA and the combination of PTd and FHA entrapped in biodegradable PLGA nanoparticles was assessed in mice following parenteral (i.p.) administration and compared to the administration of PTd and FHA in solution and empty PLGA nanoparticles. 6 groups of mice were immunised i.p. with FHA and/or PTd formulations according to Example 4 (5 µg FHA and/or PTd in 0.3 ml deionised water) or with empty PLGA nanoparticles (control) as follows:

| | |
|---|---|
| Treatment A: | empty PLGA nanoparticles |
| Treatment B: | PTd and FHA in solution |
| Treatment C: | PTd-PLGA (RG504) nanoparticles |
| Treatment D: | FHA-PLGA (RG504) nanoparticles |
| Treatment E: | PTd-PLGA (RG504) + FHA-PLGA (RG504) nanoparticles |
| Treatment F: | PTd-PLGA (RG504H) + FHA-PLGA (RG504H) nanoparticles |

Each mouse was dosed with two i.p. inoculations at weeks 0 and 4; immune responses were tested 2 weeks after the second immunisation (week 6).

Overall, very potent antibody responses were generated with antigens entrapped in these PLGA coacervate nanoparticles, with mean anti-PT serum IgG endpoint log titres of 4.3 and mean anti-FHA serum endpoint log IgG titres of 4.6. The anti-FHA antibody titres were modestly stronger with entrapped FHA compared to FHA in solution; however, the anti-PT titres for the entrapped and solution formulations were not significantly different. Formulations containing both PTd and FHA entrapped nanoparticles did not raise significantly different antibody responses compared to those generated by either entrapped antigen alone. The responses are almost identical using the two different PLGA polymers.

As shown in FIG. 10, in contrast to the $T_H1$ polarisation found upon i.p. immunisation with microparticulate entrapped antigens discussed above, the most striking feature of the antigen-specific spleen cell cytokine production was the strong polarisation of the response to $T_H2$ for all these nanoparticulate formulations. High levels of IL-5 were produced by spleen cells stimulated in vitro with FHA (1 or 5 µg/ml) or inactivated PT (1 or 5 µg/ml) or killed *B. pertussis*. The only significant antigen-specific IFN-γ production observed was against PT and killed *B. pertussis* in mice given PTd entrapped in PLGA.

A repeat experiment in which groups of 5 mice were immunised i.p. with PTd+FHA in solution, PTd+FHA in PLGA nanoparticles (formulations as outlines in Example 4) and empty PLGA nanoparticles (control) was undertaken following the same protocol as given above in this example. Spleen cell preparations from 5 mice per leg were tested individually for antigen-induced proliferation and cytokine production and serum samples from individual mice were assessed over an 8-fold dilution range for anti-PT and anti-FHA IgG.

Again, antibody responses induced with the *pertussis* antigens entrapped in PLGA nanoparticles were very strong, with end point titres in the range 4.0 to 5.0. The response to PT was almost one log stronger with the PLGA entrapped antigens when compared with the soluble antigens. The responses to FHA were stronger overall that to PT and there was not a significant difference in the end point titres in sera from mice immunised with soluble or PLGA entrapped antigens.

Strong proliferative T cell responses to FHA and killed bacteria were observed in individual spleen cell preparations from all mice immunised with PTd and FHA either in solution or entrapped in PLGA. There was no significant difference between the two immunogens. Analysis of cytokine production by spleen cells revealed very high levels of IL-5 (in the region of 1500 to 3000 pg/ml) and very modest levels of IFN-γ in response to FHA in all mice immunised with PTd and FHA, either in solution or entrapped in PLGA. FIG. 10 shows the cytokine data from the coacervated nanoparticles. The responses to inactivated *B. pertussis* were somewhat lower but were still in the region of 500 pg/ml compared with levels less than 15 pg/ml in control mice immunised with empty PLGA nanoparticles. Therefore, the overall pattern is a polarisation towards a $T_H2$ response by administration of soluble antigens or antigens entrapped in coacervated nanoparticles.

Example 12

Preparation of KLH–PLA Microparticles by a Spray Drying Method

A PLA (poly D,L lactide; molecular weight 16,000 solution: i.v.=0.27 dl/g; supplied by Boehringer Ingelheim, R203) solution in ethylacetate (5% PLA in 150 ml ethylacetate) was prepared two hours prior to use. The polymer solution was homogenised (at 24,000 rpm) using an IKA Ultra Turrax T25 homogeniser with an S1 head while the KLH antigen solution (62 mg KLH in MES (2-[n-morpholino] ethanesulfonoic acid)) was added slowly. The emulsion was cooled on ice and homogenisation was continued for 1 min. The single emulsion thus prepared was spray dried using a Büchi 191 mini spray drier with continuous stirring using a magnetic stirrer. The following parameters were used in the spray drying step:

TABLE 6

| Parameter | Value | Parameter | Value |
|---|---|---|---|
| Inlet temperature (° C.) | 60 | Aspirator (%) | 100 |
| Outlet temperature (° C.) | 45 | Pump rate* (ml/min.) | 5 |
| Flow rate | 700–800 | Pressure (mbar) | −40 |

*Pump rate was set at 25%, the actual rate of solvent pumped through varied from 5 to 6 ml/min.

The particles were collected immediately from both the collection vessel and the cyclone. The antigen-loaded microparticles were characterised according to the procedures outlined above for the previous examples. The microparticles formed according to the present invention (yield 33%) were found to be smooth and spherical in nature. The loading (µg/mg) was 7.4 with an entrapment efficiency of 91% and a D50% by laser light diffractometry of 4.6 µm. The in vitro release of KLH was found to be 10% within one hour and 49% on day 23.

Similar to the Examples above, mice were immunised with two i.p. inoculations of 20 µg KLH either entrapped in PLA microparticles or adsorbed to alum. Titres were obtained when the particles were administered to mice systemically (1×10⁵) which were comparable with those obtained in the KLH-alum group. Furthermore, the KLH–PLA particles resulted in a dominant $T_H2$ response when administered i.p. which is in contrast to that observed in the above examples for KLH–PLGA microparticles in which polarisation was towards the $T_H1$ type.

Example 13

Preparation of PTd–PLA Microparticles by a Spray Drying Method

PTd–PLA microparticles were formed by a spray drying method similar to that of Example 12 with the exceptions that, to prevent phase separation during spray drying, the homogenisation speed was increased to 24,000 rpm, the polymer viscosity was increased by using 5% R203 and the w/o emulsion was stirred during spraying. The release profile of the resultant particles was characterised by a marked burst of 50–60% in the first hour followed by a very slow release phase over a three month period of time.

Serum anti-PTd IgG levels were determined in mice immunised i.p. with 5 µg PTd in spray dried PLA microparticles and compared to immunisation with PTd–alum, empty PLA particles mixed with soluble PTd, or PTd in solution. However, no antibody or T-cell responses were obtained in mice immunised systemically with PTd–PLA.

The integrity of PTd, FHA and KLH following either the solvent evaporation (see Examples above) or spray drying processes were examined semi-quantitatively by PAGE gel analysis. More PTd remains intact when extracted from particles prepared by the solvent evaporation method relative to spray dried particles. Thus, the PTd may have been partially degraded during the spray drying process. The data suggest that while spray-drying is problematic for maintaining antigenic structure in the case of PTd, this cannot be assumed for less labile antigens and it will therefore need to be assessed on a case by case basis

What is claimed is:

1. A method of inducing a $T_H1$ polarized immune response to at least one antigen comprising parenterally administering to a subject microparticles comprising said at least one antigen entrapped or encapsulated in a biodegradable polymer, wherein said biodegradable polymer comprises a copolymer of lactic acid and glycolic acid or enantiomers thereof, and wherein said microparticles are sized such that the average diameter of said microparticles is from 2.4 µm to 4.3 µm and at least 50% of the microparticles are less than 5 µm.

2. The method of claim 1, wherein the microparticles are sized such that at least 50% of the microparticles are less than 3 µm.

3. The method of claim 1, wherein the microparticles are formed using a solvent evaporation method.

4. The method of claim 1, wherein the at least one antigen comprises a *B. pertussis* antigen.

5. The method of claim 1, wherein the parenteral administration is selected from the group consisting of intraperitoneal administration, subcutaneous administration and intramuscular administration.

6. A vaccine formulation for enhancing a $T_H1$ immune response to at least one antigen and adapted for parenteral administration comprising a pharmaceutically acceptable carrier and a pharmaceutically effective amount of microparticles comprising said at least one antigen entrapped or encapsulated in a biodegradable polymer, wherein said biodegradable polymer comprises a copolymer of lactic acid and glycolic acid or enantiomers thereof, and wherein said microparticles are sized such that average diameter of said microparticles is from 2.4 µm to 4.3 µm and at least 50% of the microparticles are less than 5 µm.

7. The vaccine formulation of claim 6, wherein the microparticles are sized such that at least 50% of the microparticles are less than 3 µm.

8. The vaccine formulation of claim 6, wherein the microparticles are formed using a solvent evaporation method.

9. The vaccine formulation of claim 6, wherein the at least one antigen comprises a *B. pertussis* antigen.

10. A vaccine formulation for enhancing a $T_H1$ immune response to at least one antigen and adapted for parenteral administration comprising a pharmaceutically acceptable carrier and a pharmaceutically effective amount of microparticles comprising at least 2 subpopulations of microparticles, each subpopulation comprising a different antigen, each antigen entrapped or encapsulated by a biodegradable polymer, comprises a copolymer of lactic acid and glycolic acid of enantiomers thereof, and wherein said microparticles are sized such that the average diameter of said microparticles is from 2.4 µm to 4.3 µm and at least 50% of the microparticles are less than 5 µm.

* * * * *